United States Patent
Liu et al.

(10) Patent No.: US 10,100,358 B2
(45) Date of Patent: Oct. 16, 2018

(54) METHODS AND COMPOSITIONS FOR REDUCING REDUNDANT MOLECULAR BARCODES CREATED IN PRIMER EXTENSION REACTIONS

(71) Applicant: Paragon Genomics, Inc., Hayward, CA (US)

(72) Inventors: Zhitong Liu, Foster City, CA (US); Guoying Liu, San Ramon, CA (US); Jeffrey Juehui Liu, Foster City, CA (US); Tao Chen, San Francisco, CA (US)

(73) Assignee: Paragon Genomics, Inc., Hayward, CA (US)

( * ) Notice: Subject to any disclaimer, the term of this patent is extended or adjusted under 35 U.S.C. 154(b) by 0 days.

(21) Appl. No.: 15/867,031

(22) Filed: Jan. 10, 2018

(65) Prior Publication Data
US 2018/0195119 A1    Jul. 12, 2018

Related U.S. Application Data

(60) Provisional application No. 62/444,704, filed on Jan. 10, 2017.

(51) Int. Cl.
*C12Q 1/68* (2018.01)
*C12Q 1/6874* (2018.01)
(Continued)

(52) U.S. Cl.
CPC ....... *C12Q 1/6874* (2013.01); *C12N 15/1065* (2013.01); *C12N 15/1068* (2013.01);
(Continued)

(58) Field of Classification Search
CPC ........................................... C12Q 1/68
See application file for complete search history.

(56) References Cited

U.S. PATENT DOCUMENTS

| 4,683,195 A | 7/1987 | Mullis et al. |
| 4,683,202 A | 7/1987 | Mullis |

(Continued)

FOREIGN PATENT DOCUMENTS

| WO | WO2006/127423 A2 | 0/2006 |
| WO | WO2005/095605 A1 | 10/2005 |

(Continued)

OTHER PUBLICATIONS

Stahlberg et al., Simple, multiplexed, PCR-based barcoding of DNA enables sensitive mutation detection in liquid biopsies using sequencing, Nucleic Acids Res. Jun. 20, 2016;44(11):e105. Epub Apr. 7, 2016.*

(Continued)

*Primary Examiner* — Aaron A Priest
(74) *Attorney, Agent, or Firm* — Shay Glenn LLP

(57) ABSTRACT

Methods, compositions, systems and kits to introduce a controlled-number of molecular barcodes onto DNA fragments by reducing redundant molecular barcodes formed in template-dependent primer extension reactions, and to find variant frequencies from both strands of DNA. The methods, compositions, systems and kits described herein may include, or include the use of, one or more single-stranded DNA specific nucleases that cleave the single-stranded regions containing unmatched base pairs in amplification products.

21 Claims, 21 Drawing Sheets

Specification includes a Sequence Listing.

(51) Int. Cl.
| | |
|---|---|
| C12N 15/10 | (2006.01) |
| C12Q 1/6848 | (2018.01) |
| C12Q 1/6806 | (2018.01) |
| C12Q 1/686 | (2018.01) |

(52) U.S. Cl.
CPC .......... *C12Q 1/686* (2013.01); *C12Q 1/6806* (2013.01); *C12Q 1/6848* (2013.01)

(56) References Cited

U.S. PATENT DOCUMENTS

| | | |
|---|---|---|
| 4,965,188 A | 10/1990 | Mullis et al. |
| 5,168,038 A | 12/1992 | Tecott et al. |
| 5,210,015 A | 5/1993 | Gelfand et al. |
| 5,399,491 A | 3/1995 | Kacian et al. |
| 5,539,082 A | 7/1996 | Nielsen et al. |
| 5,750,341 A | 5/1998 | Macevicz |
| 5,854,033 A | 12/1998 | Lizardi |
| 5,925,517 A | 7/1999 | Tyagi et al. |
| 6,174,670 B1 | 1/2001 | Wittwer et al. |
| 6,670,461 B1 | 12/2003 | Wengel et al. |
| 8,586,310 B2 | 11/2013 | Mitra et al. |
| 8,673,560 B2 | 3/2014 | Leamon et al. |
| 8,685,678 B2 | 4/2014 | Casbon et al. |
| 9,464,318 B2 | 10/2016 | Liu |
| 9,752,188 B2 | 9/2017 | Schmitt et al. |
| 2004/0185484 A1 | 9/2004 | Costa et al. |
| 2008/0014634 A1 | 1/2008 | Greener et al. |
| 2009/0123913 A1 | 5/2009 | Barany et al. |
| 2013/0261027 A1 | 10/2013 | Li et al. |
| 2014/0227705 A1 | 8/2014 | Vogelstein et al. |
| 2014/0329245 A1 | 11/2014 | Spier et al. |
| 2014/0378317 A1 | 12/2014 | Fu et al. |
| 2017/0022551 A1 | 1/2017 | Liu et al. |

FOREIGN PATENT DOCUMENTS

| | | |
|---|---|---|
| WO | WO2012/149438 A1 | 11/2012 |
| WO | WO 2015/063154 A1 | 5/2015 |

OTHER PUBLICATIONS

Chen et al.; Generation and analysis of a barcode-tagged insertion mutant library in the fission yeast schizosaccharomyces pombe; BMC Genomics; 13(1); 18 pages; retrieved from the internet (http://www.biomedcentral.com/1471-2164/13/161; Dec. 2012.

Fuhrmann et al.; Removal of mismatched bases from synthetic genes by enzymatic mismatch cleavage; Nucleic Acids Research; 33(6); 8 pages; doi:10.1093/nar/gni058; Jan. 2005.

Stoler et al.; Streamlined analysis of duplex sequencing data with du novo; Genome Biology; 17(1); 10 pages; DOI 10.1186/s13059-016-1039-4; Dec. 2016.

Allan et al.; Thermodynamics and NMR of internal GO T mismatches in DNA; Biochemistry; 36(340; pp. 10581-10594; Aug. 1997.

Babon et al.; The use of resolvases T4 endonuclease VII and T7 endonuclease I in mutation detection; in Methods in Molecular Biology; vol. 152: DNA Repair Protocols: Prokaryotic systems; Edited by P. Vaughan; © Humana Press Inc.; Totowa, NJ; pp. 187-199; Jul. 2000.

Bernard et al.; Color multiplexing hybridization probes using the apolipoprotein E locus as a model system for genotyping; Anal. Biochem.; 273(2); pp. 221-228; Sep. 10, 1999.

Casbon et al.; A method for counting PCR template molecules with application to next-generation sequencing; Nucleic Acids Res.; 39(12); 8 pages; e81.doi: 10.1093/nar/gkr217; Jul. 2011.

Crooke et al.; Section review biologicals and immunologicals: Progress in the development and patenting of antisense drug discovery technology; Expert Opinion on Therapeutic Patents; 6(9); pp. 855-870; Sep. 1, 1996.

Fu et al.; Counting individual DNA molecules by the stochastic attachment of diverse labels; Proc. Natl. Acad. Sci. USA; 108(22); pp. 9026-9031; May 31, 2011.

Gregory et al.; Targeted single molecule mutation detection with massively parallel sequencing; Nucleic Acids Res.; 44(3); 11 pages; e22. doi:10.1093/nar/gkv915; Feb. 18, 2016.

Hoffmann et al.; DNA bar coding and pyrosequencing to identify rare HIV drug resistance mutations; Nucleic Acids Res.; 35(13); 8pages; e91, doi:10.1093/nar/gkm435; ; Jun. 18, 2007.

Kanehisa ; Use of statistical criteria for screening potential homologies in nucleic acid sequences; Nucleic Acids Res.; 12(1 prt 1); pp. 203-213; Jan. 11, 1984.

Kivioja et al.; Counting absolute numbers of molecules using unique molecular identifiers; Nat. Methods; 9(1); pp. 72-74; (Author Manuscript); Nov. 20, 2011.

Leone et al; Molecular beacon probes combined with amplification by NASBA enable homogeneous, real-time detection of RNA; Nucleic Acids Res.; 26(9); pp. 2150-2155; May 1, 1998.

Lowell et al.; Heteroduplex resolution using T7 endonuclease I in microbial community analyses; Bio Techniques; 28(4); pp. 676-681; Apr. 2000.

Mackay et al.; Real-time PCR in virology; Nucleic Acids Research; 30(6); pp. 1292-1305; Mar. 15, 2002.

Mardis; The impact of next-generation sequencing technology on genetics; Treand in Genetics; 24(3); pp. 133-141; Mar. 1, 2008.

Mesmaeker et al.; Backbone modifications in oligonucleotides and peptide nucleic acid systems; Current Opinion in Structural Biology; 5(3); pp. 343-355; Jun. 1995.

Newman et al.; Integrated digital error suppression for imptoved detection of circulating tumor DNA; Nature Biotechnology; 34(5); pp. 547-555, doi:10.1038/nbt.3520; (Author Manuscript); May 2016.

Phallen et al.; Direct detection of early-stage cancers using circulating tumor DNA; Sci. Transl. Med.; 9(403); pii: eaan2415. doi: 10.1126/scritranslmed.aan2415; Aug. 16, 2017.

Schmitt et al.; Detection of ultra-rare mutations by next-generation sequencing; Proc. Natl. Acad. Sci. USA; 109(36); pp. 14508-14513; Sep. 4, 2012.

Shendure et al.; Next-generation DNA sequencing; Nature Biotechnology; 26 (10); pp. 1135-1145; Oct. 2008.

Stahlberg et al.; Simple, multiplexed, PCR-based barcoding of DNA enables sensitive mutation detection in liquid biopsies using sequencing; Nucleic Acids Res.; 44(11); pp. 1-7; e105. doi: 10.1093/nar/gkw224; Jun. 20, 2016.

Su et al.; Next-generation sequencing and its applications in molecular diagnostics; Expert Rev. Mol. Diagn.; 11(3); pp. 333-343; Apr. 2011.

Takishita et al.; Genetic diversity of microbial eukaryotes in anoxic sediment of the saline meromictic lake namako-ike (japan): on the detection of anaerobic or anoxic-tolerant lineages of eukaryotes; Protist; 158(1); pp. 51-64; Jan. 2007.

Uhlman et al.; Antisense oligonucleotides: a new therapeutic principle; Chemical Reviews; 90(4); pp. 543-584; Jun. 1, 1990.

Wang et al.; Targeted sequencing of both DNA strands barcoded and captured individually by RNA probes to identify genome-wide ultra-rare mutations; Scientific Reports; 7(1); 14 pages; 3356 DOI:10.1038/s41598-017-03448-8; Jun. 13, 2017.

Young et al.; Efficient isolation of genes by using antibody probes; Proc. Natl. Acad. Sci.USA; 80(5); pp. 1194-1198; Mar. 1983.

Zhang et al.; The impact of next-generation sequencing on genomics; J. Genet. Genomics; 38(3); pp. 95-109; (Author Manuscript) Mar. 20, 2011.

\* cited by examiner

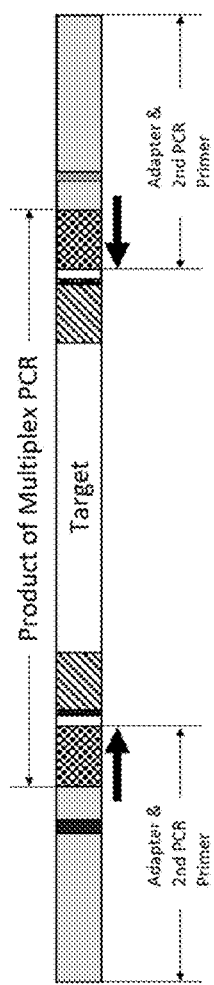
FIG. 6A
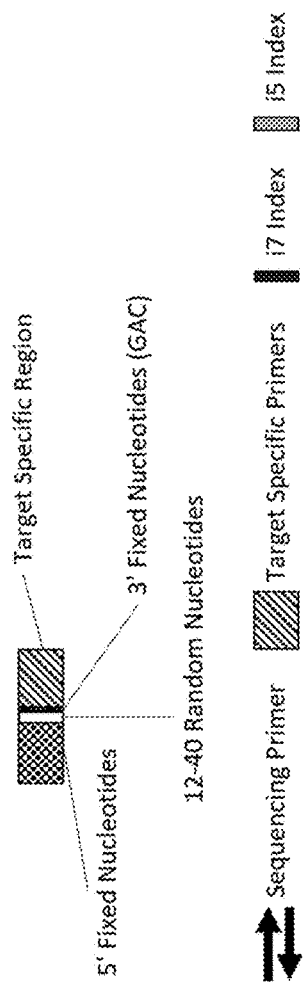
FIG. 6B
5' AATGATACGGCGACCACCGAGATCTACAC-(i5 Index)-ACACTCTTTCCCTACACGACGCTCTTCCGATC*T
5' CAAGCAGAAGACGGCATACGAGAT-(i7 Index)-GTGACTGGAGTTCAGACGTGTGCTCTTCCGATC*T
FIG. 6C

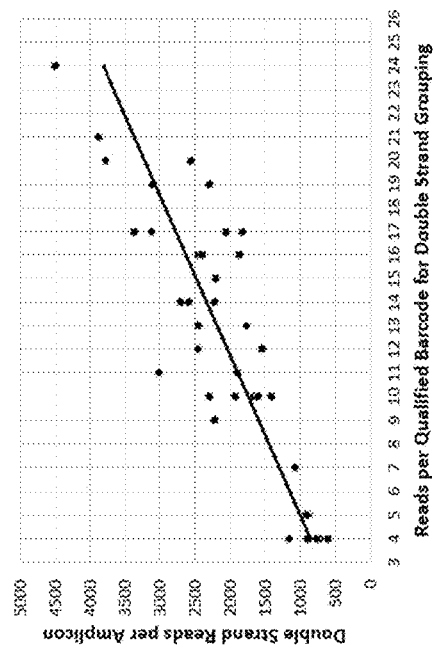
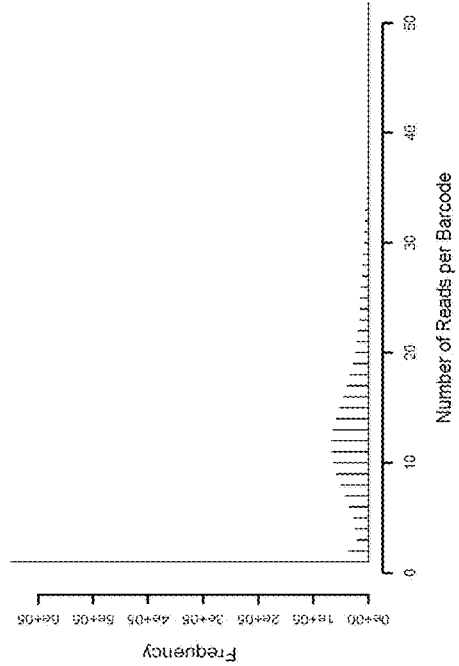
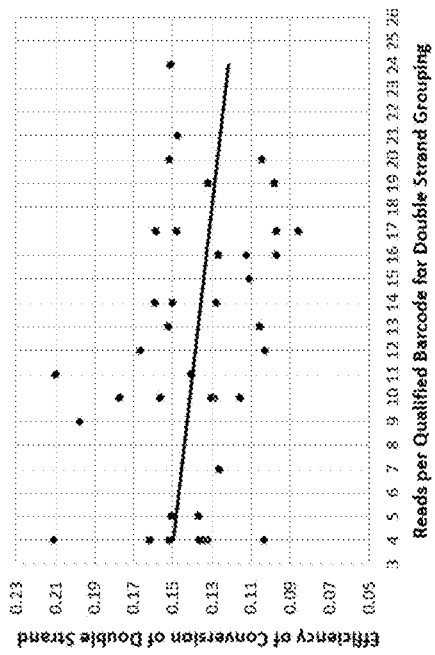
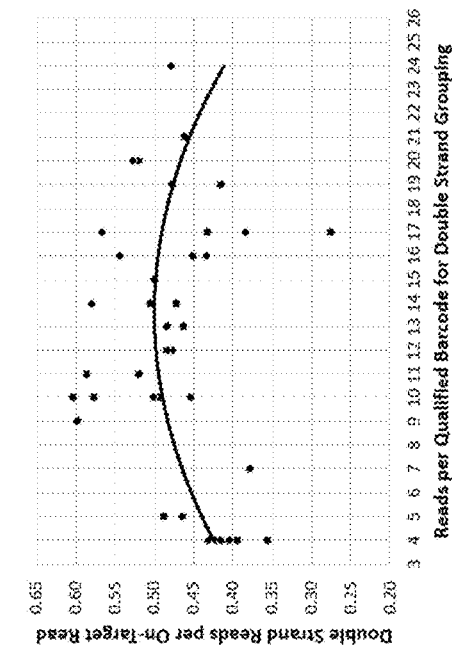
FIG. 14A
FIG. 14B
FIG. 14C
FIG. 14D

FIG. 18

| Sample ID | Yield of library in pM | Uniformity 0.3 X mean reads | Number of unique barcodes | Number of unique barcodes with 1 read | Number of unique barcodes with >= 3 reads | Number of unique barcodes with >= 5 reads | Number of unique barcodes grouped into either strand | Number of unique barcodes with >= 3 reads grouped into either strand | Paired-end raw reads | Number of reads with unique barcodes | Number of reads with unique barcodes each with >= 3 reads | Number of reads with unique barcodes grouped into either strand | Number of reads with unique barcodes each with >= 3 reads and grouped into either strand |
|---|---|---|---|---|---|---|---|---|---|---|---|---|---|
| 100 ng digested | 15750 | 97.5 | 766558 | 348592 | 244235 | 65682 | 417827 | 148348 | 5299551 | 3642164 | 2250556 | 2115780 | 1385204 |
| 100 ng undigested | 24394 | 95.0 | 1226759 | 928522 | 77251 | 12750 | 0 | 0 | 5562258 | 3309350 | 0 | 0 | 0 |

FIG. 19

| Variant Position | Variant | Expected Frequency | Digested Library | | | Undigested Library | | |
|---|---|---|---|---|---|---|---|---|
| | | | Total Reads | Variant Reads | Observed Frequency | Total Reads | Variant Reads | Observed Frequency |
| chr11_108175462_A | G | 0.10% | 10305 | 6 | 0.06% | 351 | 1 | 0.28% |
| chr12_121416622_G | C | 0.10% | 4832 | 3 | 0.06% | . | . | . |
| chr13_3292932_G | A | 0.10% | 5926 | 6 | 0.11% | 387 | 2 | 0.61% |
| chr17_41244000_C | T | 0.10% | 6611 | 10 | 0.15% | . | . | . |
| chr17_41245237_G | A | 0.10% | 2124 | 2 | 0.10% | . | . | . |
| chr17_41245466_A | G | 0.10% | 6043 | 7 | 0.12% | . | . | . |
| chr17_7579472_C | G | 0.10% | 1965 | 3 | 0.15% | . | . | . |
| chr22_24158899_A | C | 0.10% | 2451 | 3 | 0.12% | . | . | . |
| chr5_112162854_C | T | 0.10% | 4560 | 3 | 0.07% | . | . | . |
| chr7_148506396_C | A | 0.10% | 5234 | 11 | 0.23% | . | . | . |
| chr1_11288758_A | G | 0.20% | 7481 | 14 | 0.18% | . | . | . |

| ng of digested gDNA | 10 | 20 | 30 | 40 | 50 | 60 | 80 | 100 |
|---|---|---|---|---|---|---|---|---|
| Positive | 4 | 8 | 8 | 8 | 8 | 8 | 8 | 8 |
| False Negative | 4 | 0 | 0 | 0 | 0 | 0 | 0 | 0 |
| False Positive | 4 | 13 | 16 | 15 | 14 | 15 | 24 | 29 |
| Sensitivity | 50% | 100% | 100% | 100% | 100% | 100% | 100% | 100% |
| PPV | 50% | 38% | 33% | 35% | 36% | 35% | 25% | 22% |

FIG. 20A

| ng of gDNA | 10 | 20 | 30 | 40 | 50 | 60 | 80 |
|---|---|---|---|---|---|---|---|
| Positive | 22 | 23 | 23 | 23 | 23 | 23 | 23 |
| False Neg | 1 | 0 | 0 | 0 | 0 | 0 | 0 |
| False Positive | 6 | 16 | 22 | 49 | 56 | 59 | 102 |
| Sensitivity | 96% | 100% | 100% | 100% | 100% | 100% | 100% |
| PPV | 79% | 59% | 51% | 32% | 29% | 28% | 18% |

| Reference Allele (HD783) | Expected Allele | Expected Frequency | Reference Counts | Positive Allel Counts | Observed Frequency |
|---|---|---|---|---|---|
| chr12_25398284_T | C | 0.13 | 4216 | 4 | 0.10 |
| chr1_115256530_T | G | 0.13 | 3831 | 7 | 0.20 |
| chr1_115256336_T | C | 0.13 | 3200 | 5 | 0.16 |
| chr3_178936091_A | G | 0.13 | 3549 | 9 | 0.25 |
| chr7_55242464_A | AGGAATTAAGAGAAGC | 0.1 | 9686 | 312 | 3.16 |
| chr7_55248998_ATGtiCCAtiCGTtiGtiCAGtiGTGti | ATGtiCCAtiCGTGti | 0.1 | 102 | 2 | 1.96 |
| chr7_55248971_T | C | 0.1 | 156 | 3 | 1.89 |
| chr7_55255515_G | T | 0.1 | 991 | 2 | 0.20 |

FIG. 21B

| Reference Allele (NA12877) | Expected Allele | Expected Frequency | Reference Counts | Positive Allel Counts | Observed Frequency |
|---|---|---|---|---|---|
| chr11_108175462_A | G | 0.1 | 5342 | 24 | 0.47 |
| chr13_32929232_G | A | 0.1 | 2435 | 4 | 0.15 |
| chr17_41244000_C | T | 0.1 | 6111 | 27 | 0.45 |
| chr17_41244936_A | G | 0.1 | 4647 | 31 | 0.70 |
| chr17_41245237_G | A | 0.1 | 1801 | 6 | 0.36 |
| chr17_41245456_A | G | 0.1 | 4351 | 30 | 0.73 |
| chr22_24158899_A | C | 0.1 | 2319 | 3 | 0.13 |
| chr7_148506396_C | A | 0.1 | 1180 | 1 | 0.08 |
| chr10_43606587_G | A | 50 | 4936 | 1767 | 30 |
| chr20_57478207_T | C | 50 | 6340 | 3197 | 50 |
| chr22_24158895_G | A | 50 | 5043 | 2613 | 52 |
| chr12_111416622_G | C | 50 | 3902 | 1040 | 27 |
| chr5_112162854_C | T | 50 | 5800 | 2944 | 51 |
| chr5_149457678_A | G | 50 | 5967 | 3030 | 51 |
| chr3_37083740_G | A | 100 | 5042 | 5004 | 99 |
| chr17_7579472_C | G | 100 | 6774 | 6724 | 99 |
| chr5_112176756_A | T | 100 | 4935 | 4898 | 99 |
| chr5_149433586_G | T | 100 | 7875 | 7835 | 100 |
| chr5_149433597_A | G | 100 | 7769 | 7708 | 99 |
| chr7_55249063_A | G | 100 | 2673 | 2536 | 57 |
| chr1_11288758_A | G | 100 | 6660 | 6628 | 99 |

METHODS AND COMPOSITIONS FOR REDUCING REDUNDANT MOLECULAR BARCODES CREATED IN PRIMER EXTENSION REACTIONS

CROSS REFERENCE TO RELATED APPLICATIONS

This patent application claims priority to U.S. Provisional Patent Application No. 62/444,704, filed Jan. 10, 2017 (titled "METHODS AND COMPOSITIONS FOR REDUCING REDUNDANT MOLECULAR BARCODES CREATED IN PRIMER EXTENSION REACTIONS"), and herein incorporated by reference in its entirety.

This patent application may also be related to U.S. patent application Ser. No. 15/290,981, filed on Oct. 11, 2016, which claims priority as a continuation-in-part to U.S. patent application Ser. No. 15/041,644, filed on Feb. 11, 2016, now U.S. Pat. No. 9,464,318, and also titled "METHODS AND COMPOSITIONS FOR REDUCING NON-SPECIFIC AMPLIFICATION PRODUCTS", which claims priority to U.S. provisional patent applications: U.S. Provisional Patent Application No. 62/114,788, titled "A METHOD FOR ELIMINATING NONSPECIFIC AMPLIFICATION PRODUCTS IN MULTIPLEX PCR" and filed on Feb. 11, 2015; and U.S. Provisional Patent Application No. 62/150,600, titled "METHODS AND COMPOSITIONS FOR REDUCING NON-SPECIFIC AMPLIFICATION PRODUCTS" and filed Apr. 21, 2015. Each of these applications is herein incorporated by reference in its entirety.

SEQUENCE LISTING

The instant application contains a Sequence Listing which has been submitted electronically in ASCII format and is hereby incorporated by reference in its entirety. Said ASCII copy, created on Jan. 10, 2018, is named 13982-701_200_SL.txt and is 1,924 bytes in size.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods, compositions, systems and kits described herein relate to the amplification of nucleotide sequences. In particular, the methods, compositions, systems and kits described herein relate to the reduction of redundant molecular barcodes when attaching one or more molecular barcodes onto each individual DNA molecule while amplifying multiple different target DNA regions, such as during multiplex PCR. The methods, compositions, systems and kits described herein may include analyzing molecular barcodes and target DNA by high throughput sequencing (next generation sequencing, NGS).

BACKGROUND

High throughput sequencing (next generation sequencing, NGS) technology has penetrated from its early de novo sequencing into application areas that require high sensitivity and high accuracy. It has found great promises in detection of low frequency mutations, e.g., in formalin-fixed, paraffin-embedded (FFPE) DNA or ctDNA in plasma for non-invasive early diagnosis, in RNA expression, and in detection of low copy number targets (e.g., pathogens, drug-resistant variants, etc.) through deep sequencing. PCR has been an intrinsic part of NGS technology. It has been incorporated in almost all sample prep methods for NGS. Thermal stable DNA polymerase has been engineered and used as a key enzyme in the sequencing chemistry. One of major problems of high sensitivity sequencing is the presence of a vast number of random errors. These random errors are produced in PCR during sample prep, in hybridization capture through chemical modification of bases, or in the sequencing step by the error of the DNA polymerase. It may also be brought in from FFPE sample, or through oxidation from air. Usually, hundreds to thousands of random errors occur at 0.1-0.2% frequency and lower, making it impossible to find low-frequency de novo variants.

The method of using a short stretch of random (or partially random, or fixed) nucleotide sequence to label individual target molecules, thereby to eliminate PCR duplicates and reduce random base errors, has been reported since 2007 (Nucleic Acids Res 2007, 35:e91; Nucl. Acids Res. 2011 39: e81; Proc. Natl. Acad. Sci. 2011 108: 9026-9031; Nat. Methods 2011 9: 72-74). Different names, including molecular barcodes, molecular indexes, single molecular identifiers (SMI), unique identifiers (UID), unique molecular identifiers (UMI), primer ID, duplex barcodes, etc., have been used to describe this short nucleotide sequences. Molecular barcodes are usually added onto the target molecules by ligation or through primers during PCR or reverse transcription. They have been widely used in quantitative studies of gene expression through RNA sequencing, in studies of single cells, and in detecting low frequency mutations in FFPE-derived DNA and cfDNA through deep sequencing. After sequencing, they are used to trace from the amplified end molecules to their original molecules, by consolidating the sequences of the end molecules harboring identical molecular barcodes into a consensus sequence. These original molecules can be either strand of the DNA targets, or both strands. The power of labeling both strands of a DNA target with identical molecular barcodes, a technique named "duplex sequencing" (Proc Natl Acad Sci USA 2012, 109: 14508-14513; U.S. Pat. No. 9,752,188), allows a further round of deducing consensus sequence, and removing random errors. Duplex sequencing has superior sensitivity and significantly reduces the number of random errors. However, the published methods of various forms of duplex sequencing require ligation to add molecular barcodes onto the targets (Nature Medicine 2014, Nucleic Acids Res 2016, 44:e22 doi:10.1093/nar/gkv915; Nature Biotechnology, 2016, doi:10.1038/nbt.3520; Sci. Transl. Med. 2017, 9, eaan2415; Nature 2017, 7:3356, DOI:10.1038/s41598-017-03448-8;). These methods take several hours to two days of work time and numerous reagents and equipment. They demand up to several hundreds of nanograms of DNA, and have low efficiency to detect rare mutations. It seems impossible to use PCR-based methods to add identical molecular barcodes onto the double strands of the same targets for duplex sequencing. The key problem is that an original target molecule is amplified into multiple molecules, each with a different molecular barcode. These redundant barcodes make it impossible to trace themselves to the sense and antisense strand of the original double stranded DNA. For example, previous reports (U.S. Patent No. 2014/0227705, U.S. Pat. Nos. 8,741,606, 8,728,766, 8,685,678, 8,722,368, 8,715,967; Nucl. Acids Res. 2016

1-7) demonstrate methods of using 1 to 3 PCR cycles to introduce molecular barcodes onto the amplification products. These methods cannot support duplex sequencing due to that fact that either only one strand of the target DNA was labeled with molecular barcode, or redundant barcodes were produced from one original DNA molecule.

Usually tens to hundreds of amplicons are assigned with individual molecular barcode and amplified simultaneously in the same reaction vessel with a panel of primer pairs. In such a multiplex primer extension reaction, a great deal of non-specific amplification products is created between primers, between primers and template, or both. It is also necessary to remove these non-specific amplification products to make specific amplification of target sequences possible, and to further reduce the reading depth by removing the non-specific amplification products. Described herein are methods that reduce redundant molecular barcodes, while simultaneously removing non-specific amplification products.

SUMMARY OF THE DISCLOSURE

In general, described herein are methods, compositions, systems and kits for reducing redundant molecular barcodes from a template-dependent multiplex primer extension reaction. These methods, compositions, systems and kits may be useful in any reaction in which a plurality of primers each with a stretch of random nucleotides (e.g. molecular barcodes) may be used. For example, the methods, compositions, systems and kits described herein may be particularly well suited for use with multiplexed PCR and next generation sequencing.

Described herein are methods, compositions, systems and kits for reducing redundant molecular barcodes produced in a template-dependent multiplex primer extension reaction. These methods and apparatuses (e.g., kits) for performing them may include one or more enzymes to remove single-stranded DNA regions containing unmatched base pairs on the amplified DNA targets after three cycles of a primer extension reaction, thereby to remove redundant molecular barcodes. The end molecular barcodes may not be directly traced back to the original individual molecules, however, the end sequences may be grouped into a pool of sense strands and a pool of antisense strands, upon sorting the molecular barcodes at the 5' and 3' ends of the amplified DNA targets. By confirming variant frequencies in these two pools, this method can further eliminate random errors that occur on either strand. This method may be incorporated into a three-hour process. The simplicity of the method enables high efficiency and detection of rare mutations from low amount of DNA samples.

The methods and kits described herein arise from the novel finding that there is a unique time window at cycle three of multiplex primer extension reactions wherein redundant molecular barcodes can be removed using single-stranded DNA specific nucleases. These multiplex primer extension reactions involve amplification (e.g., multiplex amplification) in which an excess of a plurality of primer pairs (e.g., >6, >10, >100, >1000, >10,000, etc.) are used. The number of molecular barcodes for a specific ancestor DNA target can be reduced into one or two depending on whether the molecular barcodes are added on one end or both ends of the DNA targets. Using single-stranded DNA specific nuclease to cleave single-stranded regions at cycle two or one makes all targets un-amplifiable; while cleaving single-stranded regions at cycles larger than three leaves a large number of redundant molecular barcodes behind. Thus, although the methods and apparatuses described herein may be preferably used after a third amplification cycle, but before additional amplification cycles, they may generally be used any time after the third amplification cycle (including after additional amplification cycles).

For example, the methods described herein may include methods of reducing redundant molecular barcodes at cycle three in a multiplex primer extension reaction into two molecular barcodes for each ancestor DNA strand. An example of a method as described herein is schematically illustrated in FIG. 1. In the first step, a plurality of DNA targets (one DNA target 101 is shown) is amplified in the first round of primer extension reaction for three cycles with a plurality of pairs of primers, to produce a plurality of amplification products of DNA targets. A molecular barcode cassette (103, 103' in FIG. 1) was designed (an example of which is shown in FIG. 2A) and place it immediately upstream of the 5' end of each target specific primer in the plurality of pairs of primers. The molecular barcode cassette contains a 5' end region of fixed nucleotide sequence that serves as primer site for the second round of primer extension reaction. Immediately downstream of this 5' end region of fixed nucleotide sequence, there are 12-40 random nucleotides, serving the role as molecular barcode (105 in FIG. 1). There is a 3' end region of fixed nucleotide sequence immediately following the molecular barcode region. This molecular barcode cassette is used to validate the molecular barcode sequence later during sequencing analysis. During the first three cycles of multiplex PCR, the molecular barcode cassette does not anneal to the target sequence and stays in single strand at the either terminus, unless a complement strand is synthesized. These single-stranded regions are susceptible to the single-stranded-DNA-specific exonucleases in the next step. From each original DNA target, cycle three also produces two molecules that contain a heteroduplex region, comprised of the molecular barcode sequences, at either end, as schematically illustrated in FIG. 2B. These two molecules are derived from either strand of the original target. The 5' fixed nucleotide sequence of the molecular barcode cassette forms a stable stretch of double-stranded DNA at 5' end of the heteroduplex, and protects it from the attack by the single-stranded-DNA-specific exonucleases. The heteroduplex region is further depicted with its 5' and 3' end double-stranded DNA regions of fixed nucleotide sequences in FIG. 2C. Therefore, after cycle three, all but two descents of the same original molecule contain terminal single-stranded regions, as schematically illustrated in FIG. 2D. In the second step, the single-stranded DNA regions in the termini in the plurality of amplification products of DNA targets are cleaved with a mixture of single-stranded DNA specific exonucleases that cleaves single-stranded DNA from 5' to 3' direction and from 3' to 5' direction, making them un-amplifiable in the second round of primer extension reaction. In the third step, the DNA from the second step is amplified in a secondary primer extension reaction with a pair of primers that are complimentary to the 5' end region of fixed nucleotide sequence of the molecular barcode cassette (FIG. 1). When all terminal single-stranded DNA regions in the plurality of amplification products are cleaved after cycle three, these amplification products have only one or none double-stranded molecular barcode cassette left at the either end, and will not be amplified in the secondary amplification. Only those cleavage products that have a pair of double-stranded molecular barcode cassettes left at both ends are amplified in the secondary amplification. This results in creating two different families of offspring molecules from each ancestor double-stranded DNA target. Each family has one identical molecular barcode at either 5' end or 3' end, while other end has two different molecular barcodes. The information carried on both strands of an ancestor DNA target is carried into two independent offspring families.

After sequencing, DNA fragments are sorted into molecular barcode families by both molecular barcodes at both ends. This will lead to identification of a group of "forward" families that have one unique molecular barcode at 5' end and two unique molecular barcodes at 3' end, and a group of "reverse" families that have one unique molecular barcode at 3' end and two unique molecular barcodes at 5' end. By deducing consensus from each family, and counting variant frequencies in both forward and reverse groups, the background noises can be removed (FIG. 3).

In certain embodiments, aspects of the subject invention are drawn to methods of reducing redundant molecular barcodes at cycle 3 in an ultrahigh multiplex primer extension reaction into one molecular barcode for each ancestor DNA target. An example of one variation of a method as described herein is schematically illustrated in FIG. 4. In FIG. 4, the molecular barcode cassette is placed in one of the primers in each pair of the plurality of primers. There are 12-40 random nucleotides, serving as molecular barcode, in the molecular barcode cassette. The other primer in the plurality of pairs of primers only contains the 5' fixed nucleotide sequence that serves as primer site for next round of amplification, and 3' target-specific region. These primers are used to amplify a plurality of DNA targets in a primer extension reaction for three cycles, to produce a plurality of amplification products of DNA targets. The amplification generates a plurality of target-specific amplification products comprised of (i) double-stranded DNA fragments with matched base pairs, (ii) double-stranded DNA fragments each containing a heteroduplex region of unmatched base pairs derived from the 12-40 random nucleotides of the molecular barcode cassette, and (iii) double-stranded DNA fragments each containing single-stranded DNA regions of unmatched base pairs at either terminus, derived from the random nucleotides and the 5' end region of fixed nucleotide sequence of the molecular barcode cassette. Next, the heteroduplex region and the single-stranded DNA regions in the plurality of amplification products of DNA targets are cleaved with single-stranded DNA specific nuclease. Finally, the cleaved plurality of amplification products of DNA targets is amplified in a secondary primer extension reaction with a pair of primers that are compliment to the 5' end region of fixed nucleotide sequence of the molecular barcode cassette. When all single-stranded DNA regions and the heteroduplex regions in the plurality of amplification products are cleaved after cycle three, these amplification products have only one 5' fixed nucleotide sequence from the primers left at either end, and will not be amplified in the secondary amplification. Only those amplification products with a pair of double-stranded fixed nucleotide sequence from the primers left at both ends are amplified in the secondary amplification. This results in creating only one family of offspring molecules from each ancestor DNA target, and this family has identical molecular barcode at either 5' end or 3' end, while the other end has no molecular barcode. Basically, the information contained in one of two strands of an ancestor DNA target is carried into offspring family.

After sequencing, DNA fragments are sorted into molecular barcode families by molecular barcodes. All sequences are from either the sense strand or the antisense strand, depending on if the molecular barcodes are on forward primer or reverse primer, respectively. By deducing consensus from each family, the background noises are removed (FIG. 5).

There are eight offspring molecules created at cycle three. After cleaving the heteroduplex region and the terminal single-stranded regions, or only the terminal single-stranded regions, only one or two molecules go into the secondary amplification, respectively, thus producing one or four uniquely barcoded offspring, respectively, per original target after the secondary amplification. While reducing the number of molecular barcodes (or their combinations if molecular barcode cassette is used in both primers) to 1 or 4 per original target, this method reduces the required total sequencing reads by 8 to 2-fold. This means lower cost of sequencing, or more DNA targets can be analyzed on a specified size of flow cell.

In general, single-stranded DNA specific nucleases may be one or a combination of: T4 endonuclease VII, T7 endonuclease I, S1 nuclease, P1 nuclease, Cell nuclease, mung bean nuclease. Single-stranded DNA specific exunucleases that cleaves single-stranded DNA from 5' to 3' direction may be one or a combination of: exonuclease VII, RecJ, RecJf. Single-stranded DNA specific exnucleases that cleaves single-stranded DNA from 3' to 5' direction may be one or a combination of: exonuclease I, exonuclease VII.

Equally important to successful assigning molecular barcodes by a multiplex primer extension reaction is the efficient removal of non-specific amplification products. Any of the methods described herein may be configured to simultaneously or concurrently degrade non-specific amplification products. For example, any of the methods described herein may be used with any of the methods or apparatuses described U.S. Pat. No. 9,464,318.

In any of the methods described herein, the method may also include removing the cleaved single-stranded DNA and the degraded non-specific amplification products, leaving the substantial proportion of said plurality of target-specific amplification products with reduced number of molecular barcodes.

Any of the methods described herein may include analyzing the target-specific amplification products. Analyzing may include any appropriate method or technique, including but not limited to sequencing, such as next-generation sequencing reaction.

Amplification may include any appropriate polynucleotide amplification technique, including in particular a multiplex polymerase chain reaction (PCR).

In general, the target nucleic acids may comprise DNA or RNA, for example, genomic DNA or cDNA, DNA purified from Formalin-fixed, Paraffin-embedded (FFPE) tissue samples (FFPE DNA), cell-free DNA (cfDNA) or circulating tumor DNA (ctDNA).

As mentioned, the template-dependent primer extension reaction may include any method involving a plurality of single-stranded oligonucleotides as primers, including multiplex PCR. The primers may be single-stranded oligonucleotides; The length of primers may be from 16-100 nucleotides; the length of amplicons may be from 20 bp-1500 bp.

The target-specific primers may comprise any appropriate plurality of pairs, such as 7 pairs or more (e.g., at least 7 pairs) of target-specific primers, such as 10 pairs or more (e.g., at least 10 pairs) of target-specific primers, between 7 pairs and 100,000 pairs, between 7 pairs and 1000 pairs, between 1,000 pairs to 100,000 pairs, over 100,000 pairs of target-specific primers, etc., between 10 pairs and 100,000 pairs, between 10 pairs and 1000 pairs, etc. Although seven or more pairs are specified and may be preferable, less than seven pairs may be used (e.g., two or more pairs, three or more pairs, four or more pairs, five or more pairs, or six or more pairs, may be used).

The types of primers that may be used may include unmodified oligonucleotides, modified oligonucleotides, peptide nucleic acid (PNA); modified primers may contain one or more than one 5-methyl deoxycytidine and/or 2,6-diaminopurine, dideoxyinosine, dideoxyuridine, and biotin labeled oligonucleotides. One and/or both primers can contain barcodes or other sequences that allow for identification; one and/or both primers can contain adapter sequences.

As mentioned, any of these methods may include cleaving said single-stranded DNA regions with a single-stranded DNA specific nuclease. For example, any of these methods may include cleaving said single-stranded DNA regions with a single-stranded DNA specific nuclease comprising at least one of T4 endonuclease VII, T7 endonuclease I, S1 nuclease, P1 nuclease, Cell nuclease, mung bean nuclease, exonuclease I, exonuclease VII, RecJ, RecJf after cycle three of a primer extension reaction.

The treatment with the single-stranded DNA specific nuclease may be performed at any appropriate conditions (e.g., concentration, treatment time, temperature, etc.). In general, cleaving said single-stranded DNA regions with the single-stranded DNA specific nuclease may include exposing the plurality of amplification products to between about 0.2 Units (U) and 1000 U of one or more single-stranded DNA specific nuclease for between about 0.5 minutes and 60 minutes (e.g., 0.5 minutes for 30 minutes, 20 minutes, 15 minutes, etc.) at between 10° C. and 40° C. (e.g., more particularly between 16° C. and 37° C.).

After cycle three of a template-dependent primer extension reaction described herein, single-stranded DNA regions exist inside the regions of primers. These regions may be also described as heteroduplex region of unmatched base pairs, heteroduplex, heteroduplex DNA, heteroduplex regions, unmatched base pairs, "bubbles", unpaired regions, etc. Single-stranded DNA regions also exist at the termini of amplification products. These terminal single-stranded DNA regions may also be described as branches, forks, single-stranded forks, single-stranded tails, etc. In certain embodiments, all of these single-stranded regions described above may be cleaved to eliminate redundancy in molecular barcode. In other embodiments, only the terminal single-stranded regions are cleaved. The substantial proportion of the plurality of target-specific amplification products with reduce number of molecular barcodes may comprise 20% or more (and/or greater than 20%), 25% or more (and/or greater than 25%), 30% or more (and/or greater than 30%), 40% or more (and/or greater than 40%), 50% or more (and/or greater than 50%), 60% or more (and/or greater than 60%), 70% or more (and/or greater than 70%), 80% or more (and/or greater than 80%), 90% or more (and/or greater than 90%), 95% or more (and/or greater than 95%) of the plurality of target-specific amplification products. Thus, the single-stranded DNA specific nuclease reaction may be performed, but stopped to prevent substantial cleavage of the single-stranded regions in the target-specific amplification products. This may be adjusted by adjusting the single-stranded DNA specific nuclease treatment conditions as discussed above (e.g., about 0.2 Units (U) and 1000 U of one or more single-stranded DNA specific nuclease for between about 0.5 minutes and 60 minutes, e.g., 0.5 minutes for 30 minutes, 20 minutes, 15 minutes, etc., at between 10° C. and 40° C., e.g., more particularly between 16° C. and 37° C.). The appropriate single-stranded DNA specific nuclease buffer conditions may be used as described herein.

Also described herein are kits for performing any of the methods described herein. For example, a kit for a template-dependent primer extension reaction that reduce redundant molecular barcodes may include: a polymerase reaction mix; a plurality of target-specific primer pairs; a nuclease buffer; at least one single-stranded DNA specific nuclease; at least one pair of primers containing a common sequence; and instructions for use of said kit.

As mentioned above, the target-specific primers in the kit may comprise at least 7 pairs of target-specific primers (7 or more, 10 or more, at least to, 100 or more, 1000 or more 10,000 or more, between 7 and 100,000, between 7 and 10,000, between 7 and 1000, between 10 and 100,000, between 10 and 10,000, between 10 and 1000, between 100 and 100,000, between 100 and 10,000, between 100 and 1000, between 1000 and 100,000, between 1000 and 10,000, etc.). For example, the kit may include about 1,000 to about 100,000 target-specific primers. In some variations, the kit includes over 100,000 target-specific primers. In each primer, the target-specific region is at 3' end, a molecular barcode cassette is at 5' end. 12-40 random nucleotides serving as molecular barcode exists inside the molecular barcode cassette. This molecular barcode cassette may exist in one primer of the target-specific primer pair, or in both forward and reverse primer of the target-specific primer pair.

The kit may include any appropriate single-stranded DNA specific nuclease. For example, the single-stranded DNA specific nuclease may be Mung bean nuclease, *E. coli* exonuclease I or *E. coli* exonuclease VII.

Any of the kits described herein may also include one or more resolvase for cleaving the non-specific amplification products. For example, a kit may include a resolvase for cleaving the non-specific amplification products wherein the resolvase comprises T4 endonuclease VII.

As mentioned, kits for reducing redundant molecular barcodes from an amplification reaction are described. A kit may include at least one single-stranded DNA specific nuclease; a buffer; and instructions for use of the kit for reducing redundant molecular barcodes from said amplification reaction. The kit may further include reagents to perform a multiplex polymerase chain reaction (PCR), wherein the reagents include at least a buffer, dNTPs, a DNA polymerase, and, optionally, at least one pair of target-specific primers. The at least one pair of target-specific primers may include at least 7 pairs of target-specific primers. Further, the kit may include at least one single-stranded DNA specific nuclease. The at least one exonuclease may include Mung bean nuclease, *E. coli* exonuclease I or *E. coli* exonuclease VII.

For example, described herein are methods of reducing redundant molecular barcodes from a template-dependent primer extension reaction. Any of these methods may include: amplifying a plurality of target nucleic acids using a plurality of pairs of primers that are in a same reaction mixture for three cycles to form a plurality of double-stranded target-specific amplification DNA fragments, wherein each primer pair in said plurality of pairs of primers may include a forward primer and a reverse primer and both of the forward primer and reverse primer include a molecular barcode cassette having a molecular barcode region comprising a 12 or more (e.g., 14 or more, 15 or more, 16 or more, 17 or more, 18 or more 19 or more, 20 or more, 12-40, 12-44, 12-45, 12-47, 12-50, etc.) random nucleotide sequence that is positioned between a 5' end fixed nucleotide sequence region and a 3' end fixed nucleotide sequence region; introducing, following the third cycle, one or a mix of single-stranded DNA specific exonucleases to cleave one or more single-stranded DNA regions on a 5' terminus or a 3' terminus of double-stranded target-specific amplification DNA fragments, wherein the single-stranded DNA regions comprise unmatched base pairs at either terminus of the double-stranded target-specific amplification DNA fragments, leaving a plurality of amplification products with intact molecular barcode cassettes on both ends; and amplifying the plurality of amplification products with intact molecular barcode cassettes on both ends with a pair of primers that are complimentary to the 5' end fixed nucleotide sequence region of the molecular barcode cassette.

A method of reducing redundant molecular barcodes from a template-dependent primer extension reaction may include: amplifying a plurality of target nucleic acids using a plurality of pairs of primers that are in a same reaction mixture for three cycles to form a plurality of double-stranded target-specific amplification DNA fragments, wherein each primer pair in said plurality of pairs of primers comprises a forward primer and a reverse primer and either the forward primer or reverse primer includes a molecular barcode cassette having a molecular barcode region comprising a 12 or more (e.g., 12-40, etc.) random nucleotide sequence that is positioned between a 5' end fixed nucleotide sequence region and a 3' end fixed nucleotide sequence region, while the other primer includes the 5' end fixed nucleotide sequence region; introducing, following the third cycle, one or a mix of single-stranded DNA specific nucleases to cleave: (i) heteroduplex regions of unmatched base pairs derived from the random nucleotides of molecular barcodes of the double-stranded target-specific amplification DNA fragments, and (ii) single-stranded DNA regions on a 5' terminus or a 3' terminus of the double-stranded target-specific amplification DNA fragments, wherein the single-stranded DNA regions comprise unmatched base pairs at either terminus of the double-stranded target-specific amplification DNA fragments that are derived from the random nucleotides of the molecular barcode region and the 5' end fixed nucleotide sequence region of the molecular barcode cassette, leaving a plurality of amplification products with intact molecular barcode cassettes on either ends; and amplifying the plurality of amplification products with intact molecular barcode cassettes on either ends with a pair of primers that are complimentary to the 5' end fixed nucleotide sequence region of the molecular barcode cassette.

The unmatched base pairs at either terminus of the double-stranded target-specific amplification DNA fragments may be derived from the random nucleotides of the molecular barcode region and the 5' end fixed nucleotide sequence region of the molecular barcode cassette.

The 5' end fixed nucleotide sequence may comprise any number and type of nucleotides. For example, the 5' end fixed nucleotide sequences may be derived from adapters used in high-throughput sequencing applications.

Introducing may preferably comprise introducing the one or the mix of single-stranded DNA specific exonucleases before further amplification, e.g., immediately after the third cycle of the first round of amplification step. Alternatively, introducing one or a mix of single-stranded DNA specific exonucleases to cleave following the third cycle may be performed at any cycle after the third.

The methods described herein (and apparatuses for performing them) may use any appropriate single-stranded DNA specific exonuclease. For example, introducing the one or a mix of single-stranded DNA specific exonucleases may include introducing a resolvase, an exonuclease, multiple exonucleases, or a combination of exonucleases and nucleases, selected from the group comprising: T4 endonuclease VII, T7 endonuclease I, S1 nuclease, P1 nuclease, Cell nuclease, mung bean nuclease, exonuclease VII, RecJ, RecJf. This includes any mutants or modified versions of these that act as single-stand exonucleases.

Any of these methods may also include removing single-stranded DNA fragments that were cleaved by the one or a mix of single-stranded DNA specific exonucleases. Any appropriate removal techniques may be used and included.

In any of the methods described herein, the step of amplifying the plurality of amplification products may comprise amplifying by polymerase chain reaction, although any other amplification (or combination of amplification) techniques may be used.

Any of the methods described herein may also include analyzing the amplification products by high-throughput sequencing, and/or one or any combination of the following steps: sorting the random nucleotide sequences of the amplification products, grouping identical and similar sequences of molecular barcodes into families of molecular barcodes, validating the length and sequence of each molecular barcode in each family of molecular barcodes, and removing amplification products with disqualified nucleotide sequences of molecular barcodes. For example, the method may include high-throughput sequencing, and sorting the random nucleotide sequences of the amplification products. The method may include high-throughput sequencing, sorting the random nucleotide sequences of the amplification products, and validating the length and sequence of each molecular barcode in each family of molecular barcodes. The method may include high-throughput sequencing, sorting the random nucleotide sequences of the amplification products, validating the length and sequence of each molecular barcode in each family of molecular barcodes, and removing amplification products with disqualified nucleotide sequences of molecular barcodes.

For example, the methods described herein may include one or more of: analyzing a consensus sequence of DNA targets from each family of molecular barcodes, removing random errors from each family of molecular barcodes, finding all sequences from the sense strand, finding all sequences from the antisense strand, finding variant frequency in a pool of sense strands, finding variant frequency in a pool of antisense strands, confirmation of variant frequency in both sense and antisense strands, and removing random errors from both sense and antisense strands.

The step of amplifying the plurality of target nucleic acids may comprise performing a multiplex polymerase chain reaction (PCR). As mentioned, the plurality of target nucleic acids may comprise DNA or RNA. Any appropriate source of target nucleic acid may be used. For example, the plurality of target nucleic acids may be genomic DNA, cDNA, DNA purified from Formalin-fixed, Paraffin-embedded (FFPE) tissue samples (FFPE DNA), cell-free DNA (cfDNA) or circulating tumor DNA (ctDNA). The forward primer and a reverse primer may each includes a target-specific primer that is from 8-50 nucleotides (e.g., from 8-100, from 8-150, etc.). As mentioned, the plurality of pairs of primers may comprise at least n pairs of target-specific primers (where n is 2 or more, 3 or more, 4 or more, 5 or more, 6 or more 7 or more, 8 or more, etc., preferably 7 or more). For example, the plurality of pairs of primers may comprise between 7 pairs of target-specific primers and 1,000,000 pairs of target-specific primers.

Each primer of the plurality of pairs of primers may include a target-specific region of comprising one or more of: unmodified oligonucleotides with no chemical modifications of nucleotides, and chemical bonds and no degenerated bases. Alternatively, each primer of the plurality of pairs of primers may include a target-specific region of comprising modified oligonucleotides with one or more of: chemical modifications of nucleotides or chemical bonds, and degenerated bases. Both the forward primer and the reverse primer may contain a molecular barcode cassette.

Introducing one or a mix of single-stranded DNA specific exonucleases may comprise introducing between about 0.2 U and 1000 U of exonuclease for between 0.5 minutes and 60 minutes at between 16° C. and 37° C.

Introducing the one or a mix of single-stranded DNA specific exonucleases may comprise introducing a single-stranded DNA specific nuclease or single-stranded DNA specific exonuclease comprising one or more of: a nuclease S1, a nuclease P1, a mung bean nuclease, a CEL I nuclease, an endonuclease CEL I, an exonuclease I, an exonuclease V, an exonuclease VII, an RecJ, an RecJf, and combinations, fusions, or mutations thereof.

Also described herein are kits for reducing redundant molecular barcode configured to perform any of the methods described herein. For example, described herein are kits comprising a plurality of pairs of primers as described (e.g., including a forward and reverse primer, at least one of which includes a cassette with the random bar code sequence), a single-stranded DNA specific exonucleases, a pair of primers that are complimentary to a 5' end fixed nucleotide sequence region of the molecular barcode cassette, and one or more reagents configured for primer extension reaction and exonuclease cleavage. The one or more reagents configured for primer extension reaction and exonuclease cleavage may include buffers used in primer extension reactions and/or cleavage reactions. Any of these kits may include instructions for performing the method and using the kit.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

In FIG. 1, the schematic illustrates a method to reduce redundant molecular barcodes generated in multiplex PCR by cleaving single-stranded DNA regions at termini of amplification products. Two descends of the original DNA target with different molecular barcodes are made from a single ancestor target DNA. Each descend has one identical molecular barcode at either end of the DNA target, while two different barcodes at the other end. The arrowheads represent the 3' ends.

FIGS. 6A-6C show an example of the library structure, primer structure and primer sequences that may be used for sequencing on an Illumina platform. FIG. 6A shows an exemplary structure of a library. FIG. 6B show an example of a structure of the primers that may be used in multiplex PCR. FIG. 6C is an example of a sequence of the primers that may be used in the secondary PCR, with the 5' end fixed nucleotide sequence of molecular barcode cassette underlined. FIG. 6C discloses SEQ ID NOS 1-4, respectively, in order of appearance, corresponding to forward and reverse primers.

In FIG. 8A, a bioanalyzer graph shows libraries with digestion of the multiplex PCR products; FIG. 8B shows the results without the digestion of the multiplex PCR products.

In FIG. 9A numerous random errors were still left after single strand consensus was used to remove errors. In FIG. 9B, the majority of random errors were removed after single strand consensus was used.

In FIG. 10A, a bioanalyzer graph shows libraries with and without the digestion of the multiplex PCR products. Complete digestion was expected to produce a yield of one quarter of the undigested library. In FIG. 10B, library yield was decreased when increasing amounts of single DNA specific nuclease were used to digest the multiplex PCR products.

In FIG. 11A the method described herein was used to amplify a 629 amplicon library that contained wider distribution of GC content. No obvious GC bias was observed. The three amplicons with lowest reads in 70-80% GC range were targets of regions of TERT promoter, which were known difficult-to-amplify amplicons, yet they were still amplified. FIGS. 11B-11C are bioanalyzer graphs showing removing non-specific PCR products from 40-amplicon (FIG. 11B) and 205-amplicon libraries (FIG. 11C).

FIGS. 14A-14D illustrate the reading depth that may be required. Only molecular barcodes qualified for double strand consensus were used for the graphing. Samples with similar efficient of double strand conversion were selected to minimize the effect of insufficient molecular barcode, shown in FIG. 14A. In FIG. 14B, as expected, when higher reading depths were used, each amplicon gained more reads, however, the ratio of useful reads versus on-target reads topped when a reading depth of 12 to 16 reads per double strand barcode were reached (shown in FIG. 14C). As shown in FIG. 14D, at this range of reading depth, a standard distribution of all on-targets reads versus their associated barcodes was observed.

In FIG. 16, "20SS" represents 20 ng of DNA, consensus by single strand; "20DS" represents 20 ng of DNA, consensus by double strands. Lighter dots represent random errors, darker dots represent reference variants. Consensus was found by double strand significantly reduced the number of random errors. The number of random errors were specified by the error rate of the method. With larger amounts of DNA input, the larger amounts of random errors were observed.

FIG. 18 is table 1, showing redundant molecular barcodes in the undigested library prevented detecting the variants. Removing redundant barcodes by digestion revealed sufficient number of barcodes that can be grouped into both strands of the target DNA. The barcodes can be sued to detect rare mutations.

FIG. 19 is table 2, showing variant calls with and without redundant barcode removed. The digested and undigested libraries in table 1 (FIG. 18) were used to detect known reference variants. The numbers of detected reads in both libraries proved feasibility of our method.

FIGS. 20A-20B are table 3 and table 4, respectively, showing numbers of variant calls, sensitivity and positive predictive value of reference variants with various amounts of DNA input. In FIG. 20A, eight reference variants of HD780 detected in a 0.2% spike-in of HD780 in digested NA12877. In FIG. 20B, reference variants of NA12878 detected in a 0.2% spike-in of NA12878 in NA12877.

FIGS. 21A and 21B are table 5 and table 6, respectively, showing reference variants detected with 20 ng of DNA input. In FIG. 21A, eight reference variants of HD780 detected in a 0.2% spike-in of HD780 in digested NA12877. FIG. 21A discloses SEQ ID NOS 5-7, respectively, in order of appearance. In FIG. 21B, reference variants of NA12878 detected in a 0.2% spike-in of NA12878 in NA12877.

DETAILED DESCRIPTION

Figure 1:
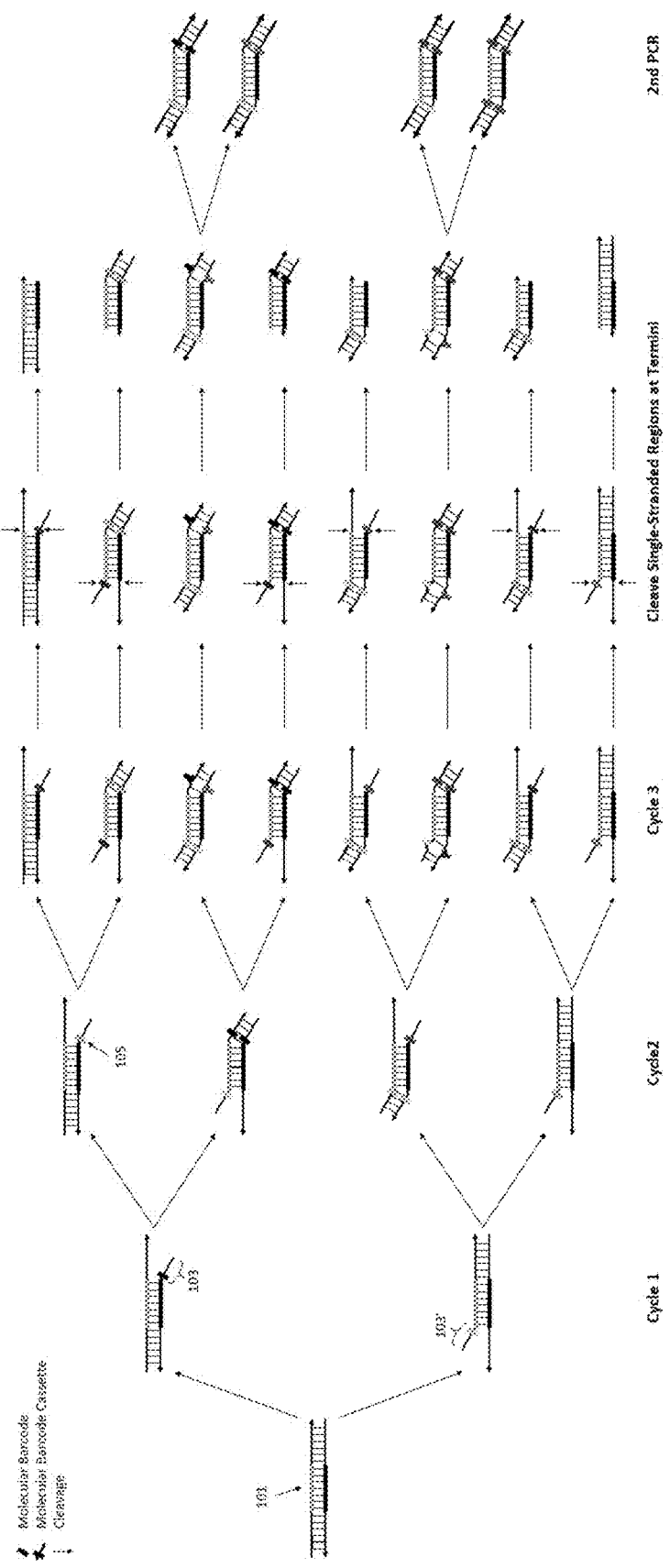
FIG. 1 illustrates one example of a mechanism of labeling DNA targets by molecular barcodes on both ends through multiplex PCR and reducing redundant barcodes.
Figure 2A:
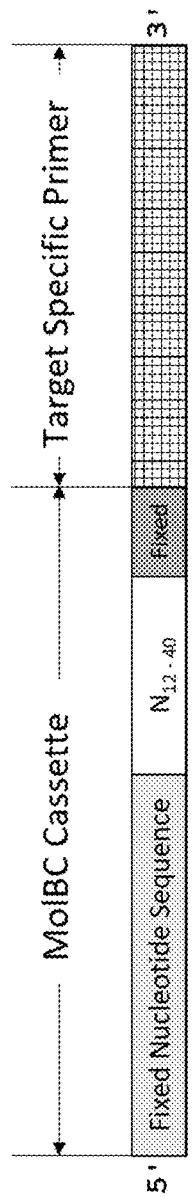
FIG. 2A illustrates an exemplary structure of a molecular barcode cassette and the downstream target specific primer region.
Figure 2C:
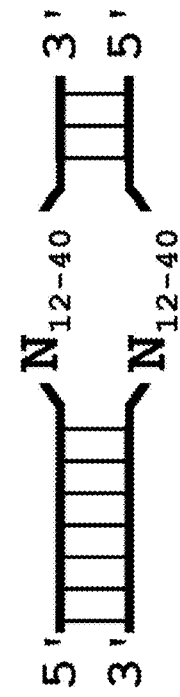
FIG. 2C shows a detailed structure of the heteroduplex region and its surrounding double-stranded DNA regions that protect the heteroduplex region from the attack of single-stranded DNA specific exonucleases.
Figure 2D:
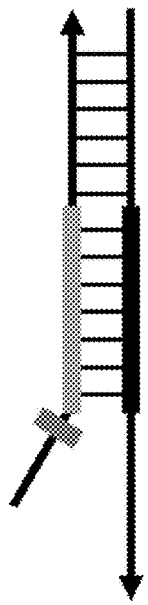
FIG. 2D is a schematic showing an amplification product with single-stranded DNA regions at one terminus. The arrowheads represent the 3' ends.
Figure 2B:
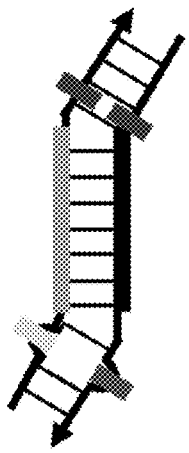
FIG. 2B is a schematic showing an amplification product with a heteroduplex region.

In general, described herein are methods, compositions, systems and kits that may be used to amplify or improve amplification of target-specific amplification products by reducing redundant molecular barcodes when amplifying multiple different nucleotide regions. These methods, compositions, systems and kits typically include or include the use of one or more single-stranded DNA specific nucleases that cleave the single-stranded regions in the amplification products at cycle three of the amplification. Unless otherwise defined, all technical and scientific terms used herein have the same meaning as commonly understood by one of ordinary skill in the art to which this invention belongs. Still, certain elements are defined for the sake of clarity and ease of reference.

Terms and symbols of nucleic acid chemistry, biochemistry, genetics, and molecular biology used herein follow those of standard treatises and texts in the field, e.g. Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, P.N.A.S, 80: 1194 (1983). Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Molecular barcode" refers to a unique of nucleotide sequence or combination thereof used to label other DNA or RNA molecules. They are usually designed as a string of totally random nucleotides (such as NNNNNNN), partially degenerate nucleotides (such as NNNRNYN), or defined nucleotides (when template molecules are limited). They have given other names, including "molecular index", "unique identifiers" (UID), "unique molecular identifiers" (UMI), "single molecular identifiers" (SMI), "primer ID", "duplex barcodes", etc. Molecular barcodes can be as long as 3 to 50 nucleotides, or even longer. They are usually synthesized as a part of the primer or adapter, for example, as a stretch of degenerated nucleotides on either 3' or 5' end of adapter. That is, the adapter part has designated nucleotide sequence, the molecular barcode part has random sequences. Molecular barcode can be single stranded, for example, as a part in primer; or double stranded, as it is in adapter. Molecular barcodes are usually added onto the targeted molecules by ligation or through primers during PCR or reverse transcription. Molecular barcodes are used in various applications including, but not limited to, RNA sequencing, studies of single cells, and detection of low frequency mutations. The main purposes of using molecular barcodes are deducing a consensus sequence from the sequences of a group of amplified descendant molecules, thereby to detect the quantity of the original target through removing amplification bias, and finding the true nucleotide sequence of the target through removing random errors and even the false targets. Consensus sequence can be deduced from the amplified sequences of either stand of the target DNA molecule, or collectively from both strands. "Collectively" means the amplified sequences from both of the sense and the antisense strand of the target DNA cannot be differentiated and have to be analyzed together; or the sequences from both strands can be differentiated but be treated as undifferentiated and analyzed together. Complementary double stranded molecular barcodes are used to label both strands of the target molecules, allowing deducing a consensus nucleotide sequence from both strand of the target DNA molecules.

"Molecular barcode family" means a group of molecular barcodes, on their corresponding target molecules, that have identical or closely related nucleotide sequence. The identical or closely related nucleotide sequence of molecular barcodes of a barcode family is also called as "unique molecular barcode". "Closely related" means any of the molecular barcodes within one specific family may have one, or two, or three, or any number of different nucleotides, or one, or two, or three, or any number of more or less nucleotides.

"Molecular barcode cassette" means a stretch of nucleotides including molecular barcode, the upstream (5' end) fixed nucleotide sequence and the downstream (3' end) fixed nucleotide sequence. The regions of the molecular barcode and the 3' end fixed nucleotide sequence are sequenced. Part or none of the 5' end fixed nucleotide sequence is sequenced. The length of the 5' end and 3' end fixed nucleotide sequences can be any number from 1 to 100 or even longer, as long as the sequencing power supports the sequencing of these sequences. Various errors happen to the sequences of molecular barcodes during the amplification of the target molecules. These errors include base changes (mutations), insertion and/or deletion of various number of nucleotides in the molecular barcode region. The 5' end and 3' end fixed nucleotide sequences are used to validate the length and the position of molecular barcodes after amplification during sequence analysis.

"Redundant molecular barcodes" means more than one molecular barcodes, each with a different nucleotide sequence, that are labeled onto the amplified offspring DNA molecules from an original target DNA molecule. That is, the amplified offspring molecules from a specific original target molecule are supposed to be labeled with identical molecule barcodes with the same nucleotide sequence, but instead, they are labeled with many different molecular barcodes with different nucleotide sequences. These different molecular barcodes are redundant barcodes. Redundant molecular barcodes are different from "barcode collision", which is that the same molecular barcodes with identical nucleotide sequence are added onto different target molecules or their amplified offspring molecules.

"Single strand consensus" means using the sequences from either the sense strand or the antisense strand, or from both of the sense and antisense strand non-discriminatorily of a target DNA molecule to deduce a consensus nucleotide sequence, or the consensus nucleotide sequence deduced from the sequences of either the sense strand or the antisense strand, or from both of the sense and antisense strand non-discriminatorily of the target DNA molecule.

"Double strand consensus" means using the sequences from both of the sense strand and the antisense strand of a target DNA molecule to deduce a consensus nucleotide sequence, or using the sequences from both of a group of the sense strands and a group of the antisense strands of the target DNA molecules to deduce a consensus nucleotide sequence; or the consensus nucleotide sequence deduced from the sequences of the sense strand and the antisense strand of the target DNA molecule, or the consensus nucleotide sequence deduced from the sequences of a group of the sense strands and a group of the antisense strands of the target DNA molecules. Double strand consensus involves, but not limited to, the finding of complementary double stranded molecular barcodes that are used to label both strands of the target molecules, or finding the molecular barcode patterns, as described in this invention, that allows differentiating the sense strands and the antisense strands of the target DNA molecules.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "TAQMAN™" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like. The one or more reagents configured for primer extension reaction and exonuclease cleavage described herein may be configured to include components that permit the primer extension and/or exonuclease cleavage to proceed. For example, one or more reagents configured for primer extension reaction and exonuclease cleavage may include buffering agents to maintain pH at a selected level during a reaction, salts, co-factors, etc.

"Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick base pairing with a nucleotide in the other strand. A stable duplex can include Watson-Crick base pairing and/or non-Watson-Crick base pairing between the strands of the duplex (where base pairing means the forming hydrogen bonds). In certain embodiments, a non-Watson-Crick base pair includes a nucleoside analog, such as deoxyinosine, 2,6-diaminopurine, PNAs, LNA's and the like. In certain embodiments, a non-Watson-Crick base pair includes a "wobble base", such as deoxyinosine, 8-oxo-dA, 8-oxo-dG and the like, where by "wobble base" is meant a nucleic acid base that can base pair with a first nucleotide base in a complementary nucleic acid strand but that, when employed as a template strand for nucleic acid synthesis, leads to the incorporation of a second, different nucleotide base into the synthesizing strand (wobble bases are described in further detail below). A "mismatch" in a duplex between two oligonucleotides or polynucleotides means that a pair of nucleotides in the duplex fails to undergo Watson-Crick bonding. "Unmatched base pairs" in a duplex between two oligonucleotides or polynucleotides means that these pairs of nucleotides in the duplex fails to undergo Watson-Crick bonding. A "heteroduplex" region in a duplex between two oligonucleotides or polynucleotides means that the nucleotides on the two strands of this region are unmatched base pairs with each other.

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Next-generation sequencing" (NGS) as used herein refers to sequencing technologies that have the capacity to sequence polynucleotides at speeds that were unprecedented using conventional sequencing methods (e.g., standard Sanger or Maxam-Gilbert sequencing methods). These unprecedented speeds are achieved by performing and reading out thousands to millions of sequencing reactions in parallel. NGS sequencing platforms include, but are not limited to, the following: Massively Parallel Signature Sequencing (Lynx Therapeutics); 454 pyro-sequencing (454 Life Sciences/Roche Diagnostics); solid-phase, reversible dye-terminator sequencing (Solexa/Illumina); SOLiD technology (Applied Biosystems); Ion semiconductor sequencing (Ion Torrent); and DNA nanoball sequencing (Complete Genomics). Descriptions of certain NGS platforms can be found in the following: Shendure, et al., "Next-generation DNA sequencing," Nature, 2008, vol. 26, No. 10, 1135-1145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11(3):333-43; and Zhang et al., "The impact of next-generation sequencing on genomics", J Genet Genomics, 2011, 38(3):95-109.

"Nucleotide" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structural Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids ("LNAs"), and like compounds. Such oligonucleotides are either available commercially or may be synthesized using methods described in the literature.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few nanoliters, e.g. 2 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("TAQMAN™"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999) (two-color real-time PCR). Usually, distinct sets of primers are employed for each sequence being amplified.

"Primer" or "target specific primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with its use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically affected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecule in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, biotin-avidin or biotin-streptavidin interactions, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

"Sample" means a quantity of material from a biological, environmental, medical, or patient source in which detection, measurement, or labeling of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The terms "upstream" and "downstream" in describing nucleic acid molecule orientation and/or polymerization are used herein as understood by one of skill in the art. As such, "downstream" generally means proceeding in the 5' to 3' direction, i.e., the direction in which a nucleotide polymerase normally extends a sequence, and "upstream" generally means the converse. For example, a first primer that hybridizes "upstream" of a second primer on the same target nucleic acid molecule is located on the 5' side of the second primer (and thus nucleic acid polymerization from the first primer proceeds towards the second primer).

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The methods provided herein can be used for the improvement of multiplex amplification (e.g., PCR) protocols or any other methods which involve a plurality of DNA primers or oligonucleotides. More particularly, the methods provided herein can be used for reducing redundant molecular barcodes in multiplex PCR protocols or any other methods which involve a plurality of DNA primers or oligonucleotides. The methods disclosed herein provide for optimized protocols for performing multiplex PCR reactions such that redundant molecular barcodes are eliminated or reduced. Overall, the methods can relate to improved methods of nucleic acid library preparation.

In one aspect, the methods provide for reducing redundant molecular barcodes from an amplification reaction. The method can involve providing a nucleic acid sample comprising at least one target nucleic acid. The nucleic acids can be RNA or DNA. The DNA can be genomic DNA, cDNA, cfDNA, ctDNA or any combination thereof. The DNA can be single-stranded or double-stranded. The DNA can be derived from a eukaryotic cell, an archaea cell, a bacterial cell, a mycobacterial cell, a bacteriophage, a DNA virus, or an RNA virus, or converted from RNA. In some cases, the DNA can be derived from a mammal. In some cases, the DNA can be derived from a human. The DNA can be unmodified, or can be modified (e.g., methylated, glycosylated, etc.). The nucleic acids can be used in an amplification reaction. The nucleic acids used in the amplification reaction can comprise at least one target nucleic acid sequence. A target nucleic acid sequence generally refers to a nucleic acid sequence that is targeted and enriched, for example, with target-specific primers, in a mixture of nucleic acids. The amplification reaction can be any method involving hybridizing a plurality of DNA primers or oligonucleotides to their corresponding targets. The amplification can be a polymerase chain reaction (PCR). In one example, the amplification reaction is a multiplex PCR. In other examples, the amplification reactions can be amplification by ligation extension, nested multiplex PCR, whole genome amplification, whole exon amplification, or isothermal amplification reactions with more than one pair of oligonucleotides, etc. Serving as one example, multiplex PCR provides for the simultaneous amplification of a plurality of target nucleic acids in a single vessel (i.e., tube, well, vial, and the like) to generate a plurality of amplicons. Multiplex PCR generally involves the use of a plurality of target-specific primer pairs that can selectively enrich a plurality of target nucleic acids. The plurality of target-specific primer pairs can be from 7 primer pairs to over 100,000 primer pairs. In one case, the plurality of target-specific primer pairs comprises at least 7 pairs of target-specific primer pairs. In another case, the plurality of target-specific primer pairs comprises from about 7 to about 100 primer pairs. In another case, the plurality of target-specific primer pairs comprises from about 100 to about 1,000 primer pairs. In yet another case, the plurality of target-specific primer pairs comprises from about 1,000 to about 100,000 primer pairs. In a further case, the plurality of target-specific primer pairs comprises over 100,000 primer pairs.

Primers can comprise unmodified bases and/or phosphodiester bonds, or modified bases and/or phosphodiester bonds, unprotected 5' ends, or protected 5' ends, 5' phosphorylated, or 5' unphosphorylated ends. Primer pairs can be designed such that the amplicon length can be from under 100 to over 1000 base pairs. Multiplex PCR reactions as envisioned in this disclosure can be performed by thermostable DNA polymerases commonly used in PCR reactions. Thermostable DNA polymerases can be wild-type, can have 3'→5', 5'→3', or both 3'→5' and 5'→3' exonuclease activity, or can be a mixture of thermostable polymerases for higher fidelity, or can synthesize long amplicons, or have faster synthesizing rate. An example of a suitable thermostable DNA polymerase can be Taq DNA polymerase. The thermal profile (temperature and time) for the PCR can be optimized, the primer concentration can also be optimized to achieve the best performance. Finally, any additives that can promote optimal amplification of amplicons can be used. These additives include, without limitation, dimethyl sulfoxide, betaine, formamide, Triton X-100, Tween 20, Nonidet P-40, 4-methylmorpholine N-oxide, tetramethylammonium chloride, 7-deaza-2'-deoxyguanosine, L-proline, bovine serum albumin, trehalose, and T4 gene 32 protein.

The methods as disclosed herein can further involve contacting the amplification reaction with a single-stranded DNA specific nuclease for cleaving single-stranded DNA regions. As used herein, the term "contacting" equates with introducing such enzyme to a pre-existing mixture as described herein. The methods of the present disclosure can use a variety of single-stranded DNA specific nucleases that can recognize and cleave single-stranded DNA regions. The plural form will be used herein to refer to enzymes that bind to and cleave aberrant DNA structures. The single-stranded DNA regions include, without limitation, branched DNAs, Y-structures, heteroduplex loops, single stranded overhangs, mismatches, and other kinds of non-perfectly-matched DNAs. In some examples, the single-stranded DNA specific nuclease can reduce the amount of single-stranded DNA regions in the amplification reaction without reducing the amount of target-specific amplification products that do not contain single-stranded DNA regions. In other examples, both single-stranded DNA regions and target-specific amplification products can be reduced. In some cases, the amplification reaction can be substantially free of single-stranded DNA regions. Substantially free of single-stranded DNA regions can mean that the amount of single-stranded DNA regions in the amplification reaction have been reduced by greater than 50%, 60%, 70%, 80%, 85%, 90%, 91%, 92%, 93%, 94%, 95%, 96%, 97%, 98%, 99%, up to 100%.

Examples of single-stranded DNA specific nucleases that can be utilized to cleave single-stranded DNA regions in the methods provided herein include, without limitation, bacteriophage Holliday junction resolvase T7 endonuclease I; T4 endonuclease VII; flap endonuclease (FEN); *E. coli* endonuclease V, *Thermotoga maritima* endonuclease V; S1 nuclease; P1 nucleases; mung bean nuclease; CEL I; SP1 nuclease; exonuclease VII; RecJ; RecJf. In specific examples, the single-stranded DNA specific nuclease can be T4 endonuclease VII, or mung bean nuclease, or exonuclease VII, or RecJ, or RecJf. It should be understood that essentially any single-stranded DNA specific nuclease or its mutant that can perform the methods of the disclosure as described herein is envisioned.

In some cases, the methods can involve removing the cleaved single-stranded DNA regions from the amplification reaction. In other cases, the cleaved single-stranded DNA regions may be further digested into small oligonucleotides and nucleotides by E. coli. exonuclease I.

In some cases, the amplification products described herein can be used to prepare libraries for next-generation sequencing. The common sequences in the primer pairs are identical to part of adapters useful for next-generation sequencing applications. The adapters can be sequencing adapters useful on a next-generation sequencing platform (e.g., Illumina TruSeq adapters). For example, the methods of the invention are useful for next-generation sequencing by the methods commercialized by Illumina, as described in U.S. Pat. No. 5,750,341 (Macevicz); U.S. Pat. No. 6,306,597 (Macevicz); and U.S. Pat. No. 5,969,119 (Macevicz).

Particular reference will now be made to specific aspects and figures of the disclosure. Such aspects are provided by way of example only. Numerous variations, changes, and substitutions will now occur to those skilled in the art without departing from the disclosure.

EXAMPLES

Example 1. Method of Dual Molecular Barcodes

Figure 3:
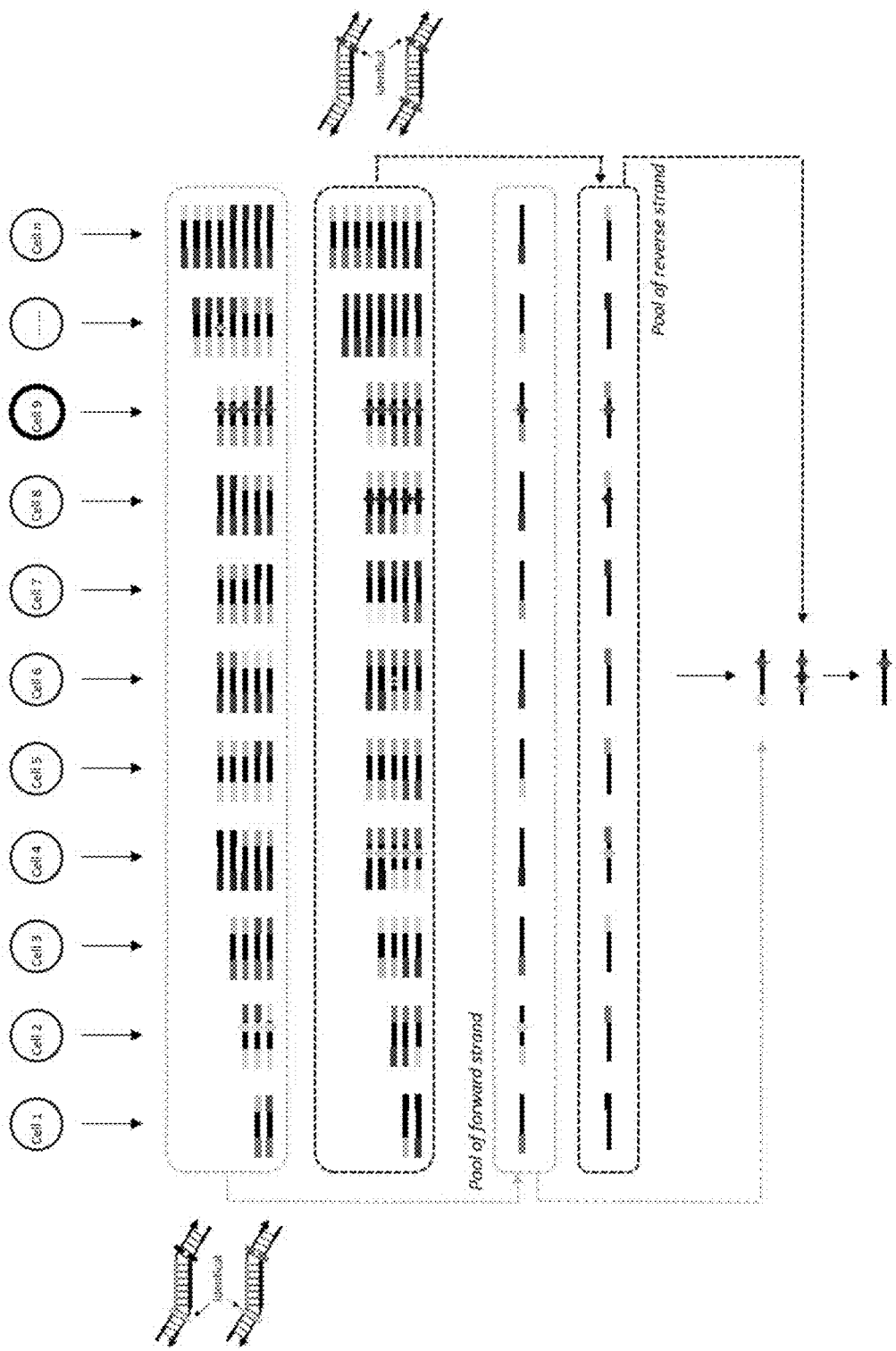
FIG. 3 illustrates one example of a mechanism of variant calling by double strand consensus. A schematic illustrates sorting molecular barcode families by both molecular barcodes at both ends, deducing consensus from each family, and counting variant frequencies in both forward and reverse pools. For all forward strands, each molecular barcode family has identical 5' molecular barcode, but two different 3' molecular barcodes. For all reverse strands, each molecular barcode family has identical 3' molecular barcode, but two different 5' molecular barcodes. A consensus sequence is further derived from the forward and reverse strand groups, while random errors are removed.

To demonstrate the feasibility of our method of removing redundant molecular barcodes from a primer extension reaction involving molecular barcodes on BOTH primers (depicted in FIG. 1), and the consequent removing of random errors and variant calling from both strands of target DNA (FIG. 3), the effect of single-stranded DNA specific exonuclease on the yield of DNA libraries was tested, and the subsequent variant calling after sequencing the libraries.

To enable a library to be sequenced in Illumina sequencing machines, the library structure was designed as shown in FIG. 6A. DNA targets were amplified with a plurality of pairs of primers (also referred as primer panel or panel) in the multiplex PCR reaction for three cycles. After removing redundant barcodes, the products of multiplex PCR were further amplified in the second round of PCR with a pair of primers to produce the library. A primer panel containing 40 pairs of primers (40 plex) was used. As described in the summary, each primer contained a 3' end target specific region that specifically amplifies the target DNA, and a 5' end molecular barcode cassette (FIG. 6B). The 5' end fixed nucleotide sequences of the molecular barcode cassette were complimentary to the pair of primers used in the secondary PCR. The 12-40 nucleotide-long random sequence served as molecular barcodes to label individual target molecules. The fixed nucleotide sequences on both side of the molecular barcode were used to validate the length of molecular barcodes during sequence analysis after sequencing. The pair of primers used in the secondary PCR reaction, as well as the 5' end fixed nucleotide sequence of molecular barcode cassette (underlined), is shown in FIG. 6C. The 3' end fixed nucleotide sequence used in this test was GAC. The length of the random nucleotide region was 12 nucleotides.

Template DNA, NA12878 and NA18507, was purchased from Coriell Institute. We mixed these two reference DNA at 0.2% NA12878 in NA18507 (0.2% NA12878/NA18507) by weight, and made the total concentration at 40 nanograms per microliter (ng/µl). Other reference DNA was also used. These include NA12877 from Coriell Institute, HD780 from Horizon Discovery, and Seraseq ctDNA Mutation Mix v2 (purified DNA) (Catalog Number 0710-0143) from SeraCare.

Figure 7:
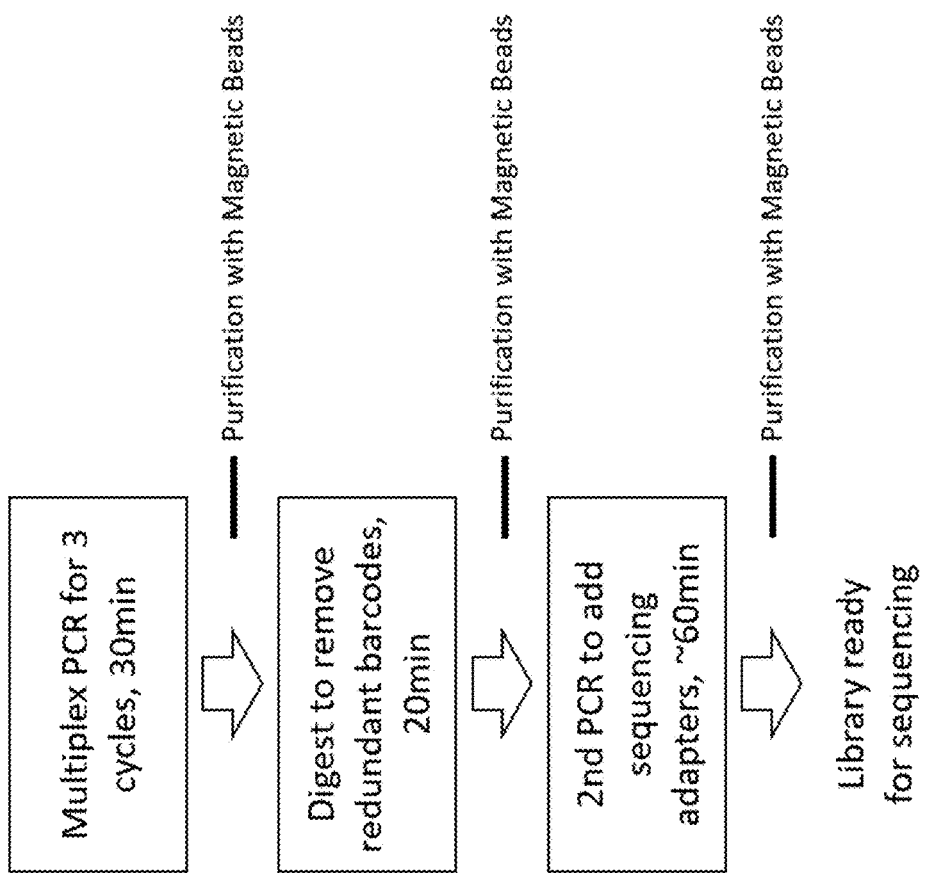
FIG. 7 shows an example of a workflow of the method described herein.

The workflow is depicted in FIG. 7. 100 ng of 0.2% NA12878/NA12877 mixed DNA was amplified with 25 nM each of the 40 pairs of primers by PCR. The reagents and the method of multiplex PCR were provided by Paragon Genomics Inc. (CleanPlex™ Targeted Library Kit, SKU: 816001), similar to what was described in U.S. patent application Ser. No. 15/290,981. The multiplex PCR was stopped after three cycles. Following purification of amplification products with magnetic beads (an example of which is described in the User Guide of CleanPlex™ Targeted Library Kit), the DNA was treated with 2 µl of the digestion reagent (e.g., CP Digestion Reagent containing T4 endonuclease VII from the CleanPlex™ Targeted Library Kit) supplemented with 2 units of E. coli exonuclease VII at 37° C. for 20 minutes. The reaction was purified with magnetic beads, and amplified again for 21 cycles with a pair of second amplification primers. A second library was made alongside with the one described above, this library was treated with 2 µl of digestion reagent without exonuclease (e.g., with no supplement of E. coli exonuclease VII), referred to as "undigested library".

Figure 8A:
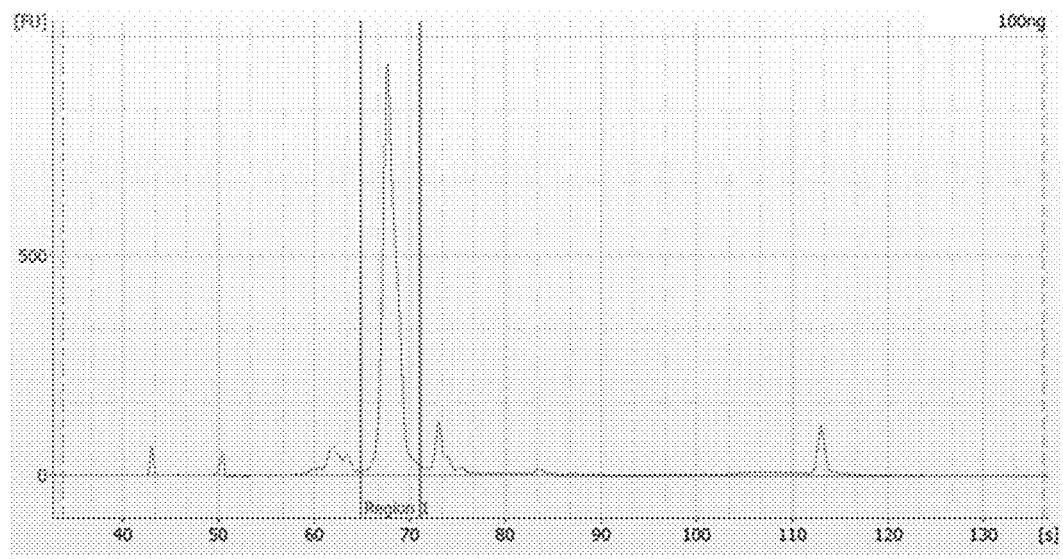
FIGS. 8A-8B illustrate the reduction in redundant molecular barcodes for double strand consensus.
Figure 8B:
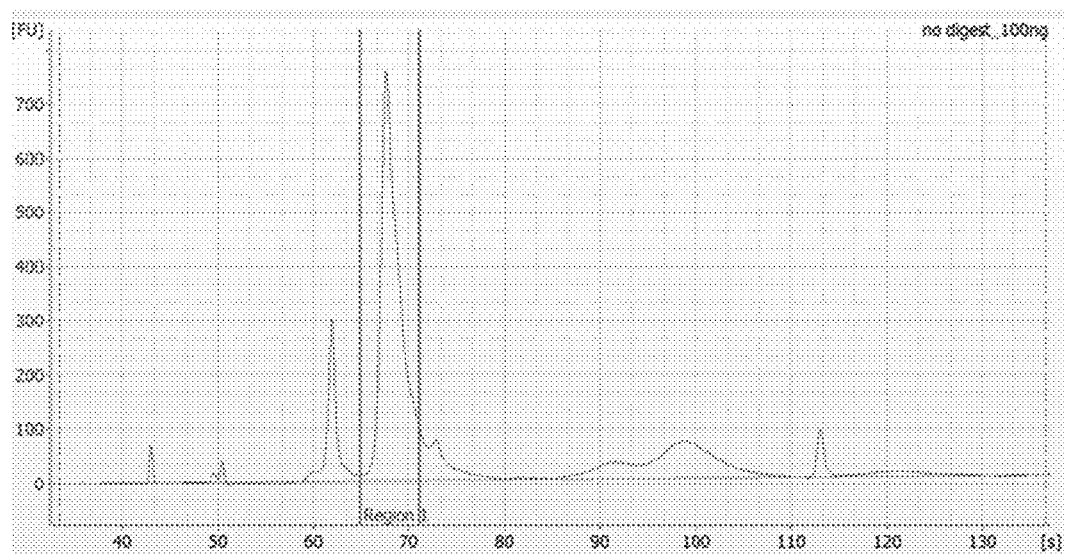

The size, concentration and purity of these libraries were assayed in a 2100 BioAnalyzer instrument (Agilent Technologies, catalog number G2938B). 1 µl of each library was assayed with a high sensitivity DNA analysis kit (Agilent Technologies, catalog number 5067-4626), according to the methods provided by the supplier. The results are presented in FIGS. 8A-8B. As expected, the concentration of the library treated with E. coli exonuclease VII was 15750 pM, which was 64.6% of the undigested library (24394 pM), indicating the removal of about half of the redundant molecular barcodes (FIG. 1).

These libraries were sequenced on an Illumina NextSeq sequencer with a high output flowcell at 2×150 bp read length. After sequencing, the sequence data were filtered to remove those that did not mapped onto the human reference genome, and those that did not mapped onto the defined targets of amplification. Each library was sort by the sample indexes, each of the 40 DNA targets (amplicons) was further sorted by their sequence. Within each amplicon, molecules derived from different cells were further sorted by the molecular barcodes. This leaded to the formation of "families" by molecular barcodes. Each family contained a different number of members (also referred to as "reads"). All of the reads within a specific family had identical molecular barcodes (referred to as "unique molecular barcode" of each family). In order to maximize the number of reads in each family while maintain the fidelity of molecular barcodes, the molecular barcodes were further analyzed by their sequence and length. Any molecular barcode that differed from another one by two or more nucleotides in sequence or length was not placed into the same family. In other words, any molecular barcode that differed from another one by only one nucleotide in sequence or length was placed in the same family. The members of each family were used to deduce a consensus sequence of the target DNA. The results are shown in table 1 (FIG. 18). Both libraries had similar uniformities (97.5% of digested and 95% of undigested) at 0.5× mean reads, and similar paired-end raw reads (5.3 million of digested and 5.6 million of undigested). However, the undigested library had 1.6-fold greater number of unique barcodes than that of the digested library. With similar number of raw reads, the library with redundant molecular barcodes is expected to have a larger number of barcode families with less number of members, and fewer families with larger number of members, than the library without redundant barcodes. This was seen with the undigested library that had 2.7-fold number of barcode families with one member, 0.3-fold number of barcode families with three members, and 0.2-fold number of barcode families with five members than those of the digested library. Further, for the undigested library, it was impossible to group the barcodes into sense and anti-sense strand by the sequence of the molecular barcodes because of the complex combinations of barcodes. In contrary, the digested library allowed the molecular barcodes to be grouped into sense strand and anti-sense strand of the original DNA targets.

We identified 11 variant positions in NA12878 that differ from those in NA18507. These variant points were expected to be identified at variant frequency of 0.1% (0.2% for chr1_11288758_A) in the digested library made with 0.2% NA12878/NA18507. We sorted the molecular barcodes into sense and anti-sense strand of each original DNA targets, removed random errors by making consensus sequence from both strands of the target DNA, and calculated the variant frequencies of each point. Shown in FIG. 19 (table 2), all of these 11 points were identified, the detected variant frequencies were close to those expected (0.1%).

Molecular barcodes are used to remove random errors generated during library making and sequencing process. We investigated the effect of grouping molecular barcodes into both strands of target DNA on reducing the number of random errors. Shown in FIG. 9, we compared the number of random errors found when the reads were sorted by molecular barcodes directly from either strand of target DNA, and those from both strands of each target DNA. We saw the number of random errors were significantly reduced when molecular barcodes were sorted into both strands of the target DNA molecules.

The method was successfully used to reduce redundant molecular barcodes, to reduce random errors, and to detect all expected variant points around the expected variant frequencies. It should be noted that this method, for the first time, makes it possible to use multiplex PCR to label DNA molecules with non-redundant molecular barcodes, and at the same time, allow variant calling from both sense and anti-sense strand of the target DNA molecules.

Example 2. Method of Single Molecular Barcode

Figure 4:
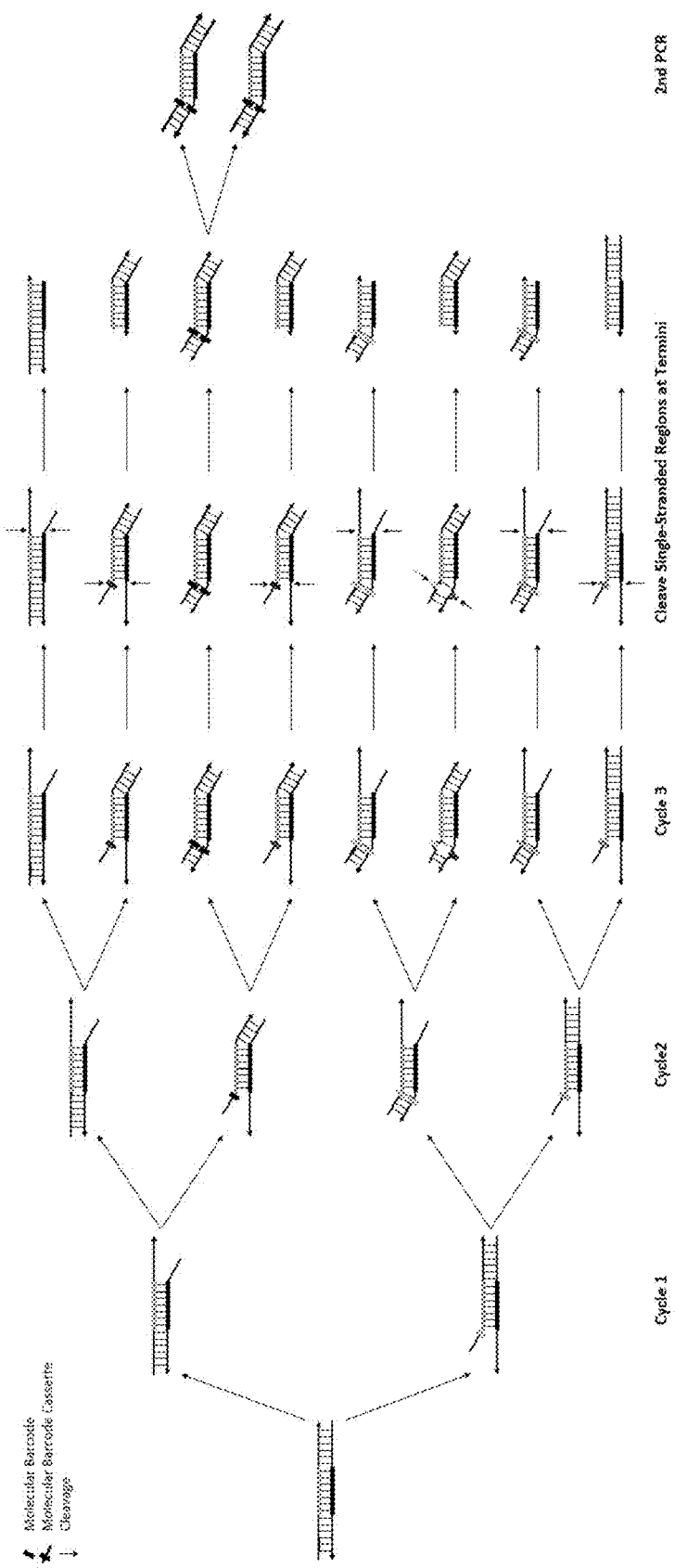
FIG. 4 shows an example of a mechanism of labeling DNA targets by molecular barcodes on one end through multiplex PCR and reducing redundant barcodes. The schematic in FIG. 4 illustrates a method of the present disclosure to eliminate redundant molecular barcodes generated in multiplex PCR by cleaving single-stranded DNA regions. Only one offspring of the original DNA target with molecular barcode on either side is made from an ancestor target DNA. The arrowheads represent the 3' ends of DNA targets.
Figure 5:
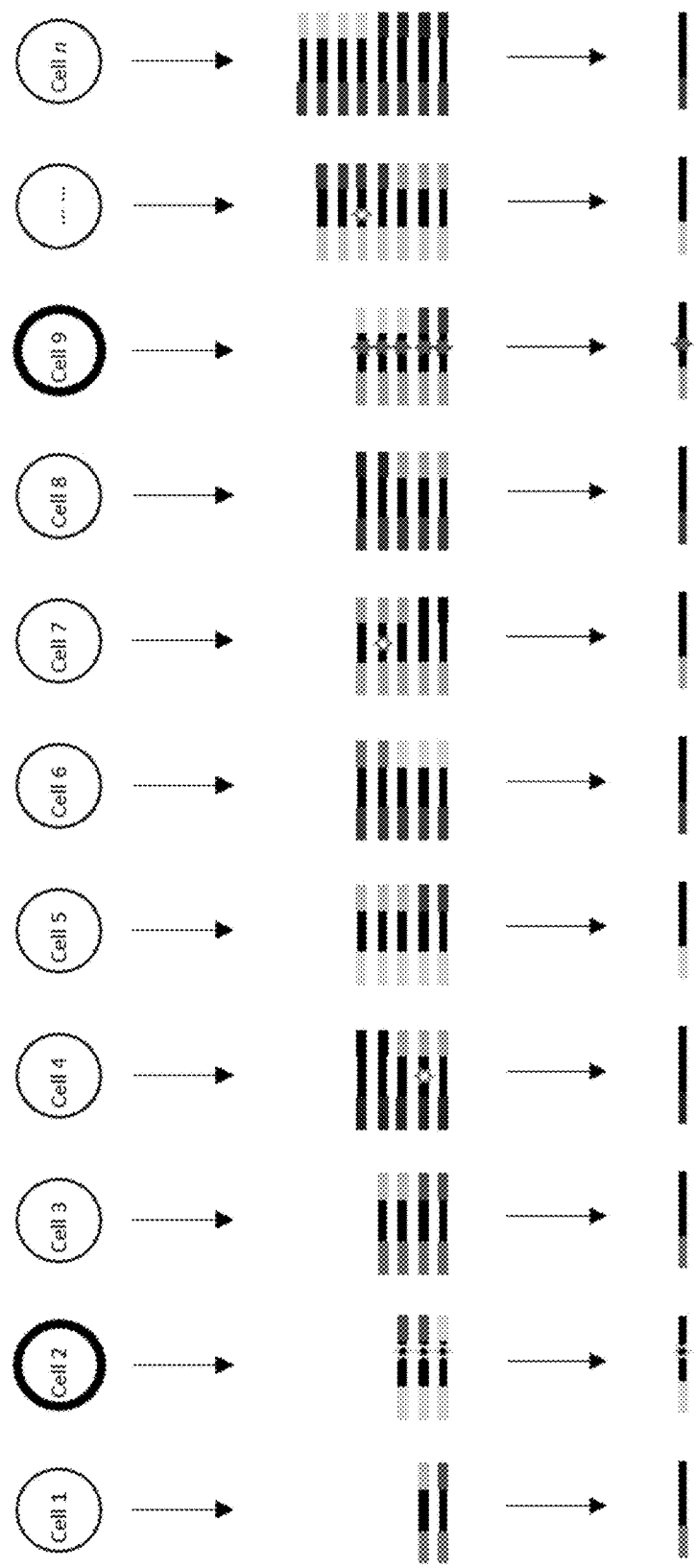
FIG. 5 shows an example of a mechanism of variant calling by single strand consensus. Sequencing reads are sorted by the molecular barcodes on one end, consensus sequences are deduced from each barcode family.

In this example, the feasibility of the method to remove redundant molecular barcodes from a primer extension reaction involving molecular barcode on ONE primer was demonstrated, as depicted in FIGS. 4 and 5. A primer panel containing 205 pairs of primers were used to amplify corresponding DNA regions in 0.2% NA12878/NA18507. Each primer of these 205 pairs of primers contained a 3' end target-specific nucleotide sequence and a 5' fixed nucleotide sequences. The 5' fixed nucleotide sequences were complimentary to the pair of primers used in the secondary PCR. Each forward primer additionally contained a 10-nucleotide random sequence, serving as molecular barcode, between the 3' end target-specific sequence and the 5' end fixed nucleotide sequence. 100 ng of 0.2% NA12878/NA18507 and 25 nM each of the 205 pairs of primers were used in a multiplex PCR reaction. The reagents and the method of multiplex PCR were provided by Paragon Genomics Inc. (CleanPlex™ Targeted Library Kit, SKU: 816001). The multiplex PCR was stopped after three cycles. Following purification of amplification products with magnetic beads as described by the User Guide of CleanPlex™ Targeted Library Kit, the DNA was treated with 2 µl CP Digestion Reagent (from CleanPlex™ Targeted Library Kit) at 37° C. for 10 minutes, then with 5 µl of Mung bean nuclease buffer and 20 units of Mung bean nuclease (New England Biolab) at 30° C. for 30 minutes. The reaction was stopped with 2 µl Stop buffer, purified with magnetic beads, and amplified again for 16 cycles with a pair of second amplification primers, as specified by the User Guide of CleanPlex™ Targeted Library Kit. A second library was made alongside with the one described above, this library was only treated with 2 µl of CP Digestion Reagent (referred to as "undigested library").

Figure 10A:
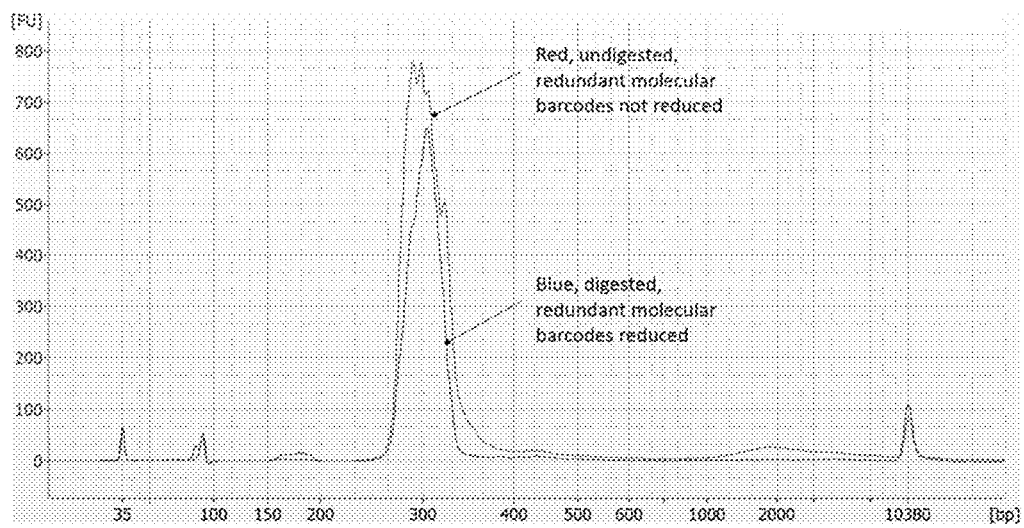
FIGS. 10A-10B illustrate reducing redundant molecular barcodes for single strand consensus.
Figure 10B:
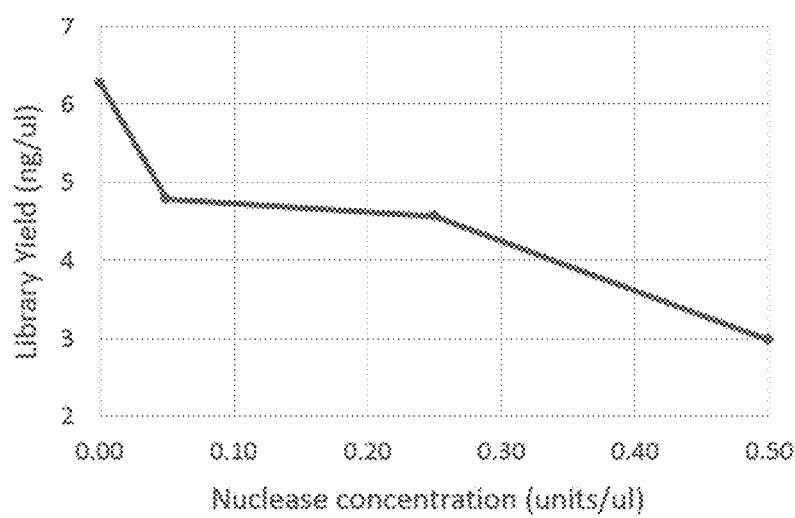

The size, concentration and purity of the library were assayed in a 2100 BioAnalyzer instrument (Agilent Technologies, catalog number G2938B). 1 µl of the library preparation obtained in the previous step was assayed with a high sensitivity DNA analysis kit (Agilent Technologies, catalog number 5067-4626), according to the methods provided by the supplier. Mung Bean nuclease digested library had a concentration of 19248 pM, which was significantly lower than 40421 pM of the undigested library (FIG. 10A). However, the concentration ratio (1 to 2.1) of these two libraries was not close to 1 to 4, as expected from FIG. 4. This could be caused by incomplete digestion by Mung Bean nuclease, or over amplification of the libraries in the second PCR. To demonstrate that the yield of digested library was dependent upon the treatment by Mung Bean nuclease, a series of libraries were made by using different amounts of Mung Bean nuclease. Progressively lower yields were obtained when increasing amounts of Mung Bean nuclease were used (FIG. 10B).

Figure 9A:
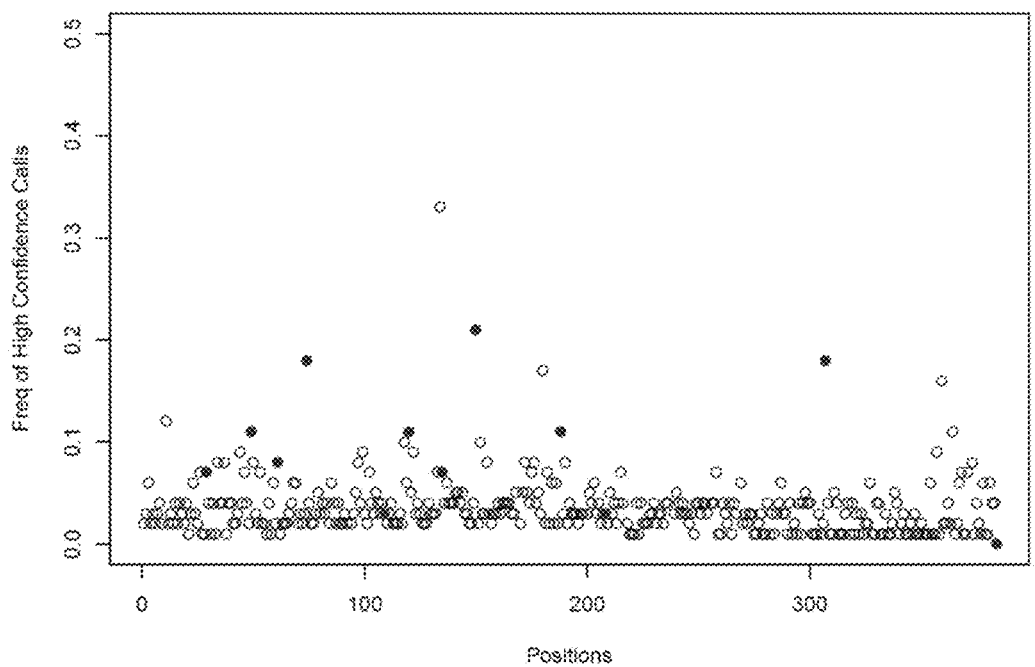
FIGS. 9A-9B illustrate random error removing by single strand consensus and double strand consensus. The solid dots represent the known reference variants. The open dots represent the random errors.
Figure 9B:
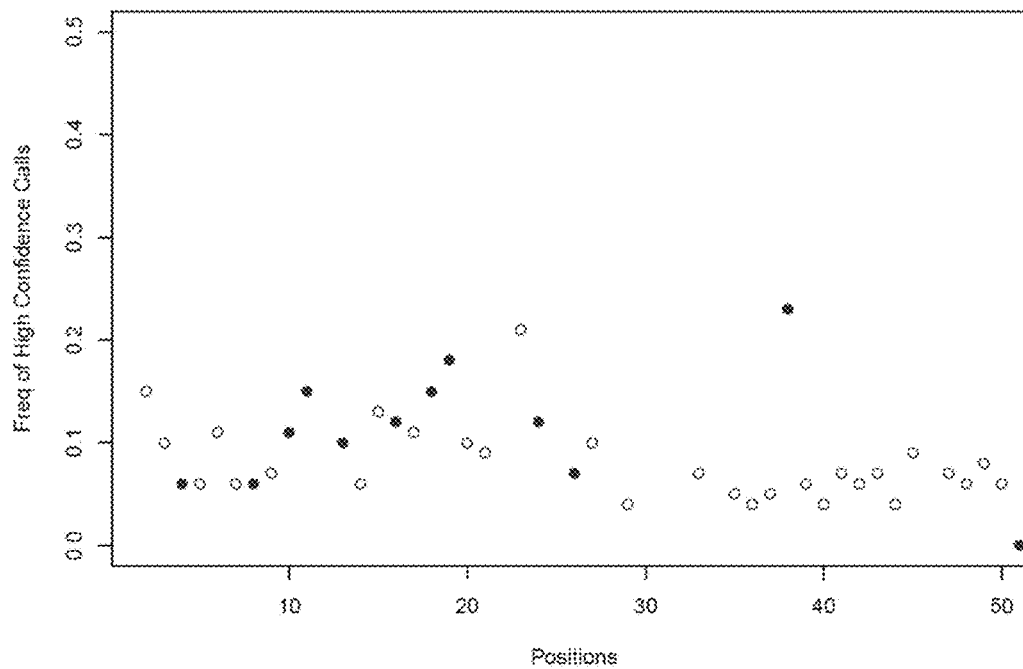

The Mung bean nuclease digested library was sequenced and analyzed by the same method as described in Example 1, except that molecular barcodes were sorted by only one strand of target DNA. All of 11 variant points were identified, and the detected variant frequencies were close to 0.1%. However, the number of random errors was high, similar to that of the library in Example 1 with molecular barcodes sorted using only one strand of target DNA (FIG. 9). This indicated that even though the number of redundant molecular barcodes was reduced, it required barcoding and analyzing both strands of the target DNA to effectively remove random errors.

So far, we described our method of using multiplex PCR to make libraries with non-redundant molecular barcodes, analysis of these libraries to remove random errors and calling variants at 0.1% frequency. In the following examples, we used the same method to make, sequence and analyze a variety of libraries to address the different aspects of the method.

Example 3. Uniformity of Amplification

Figure 11A:
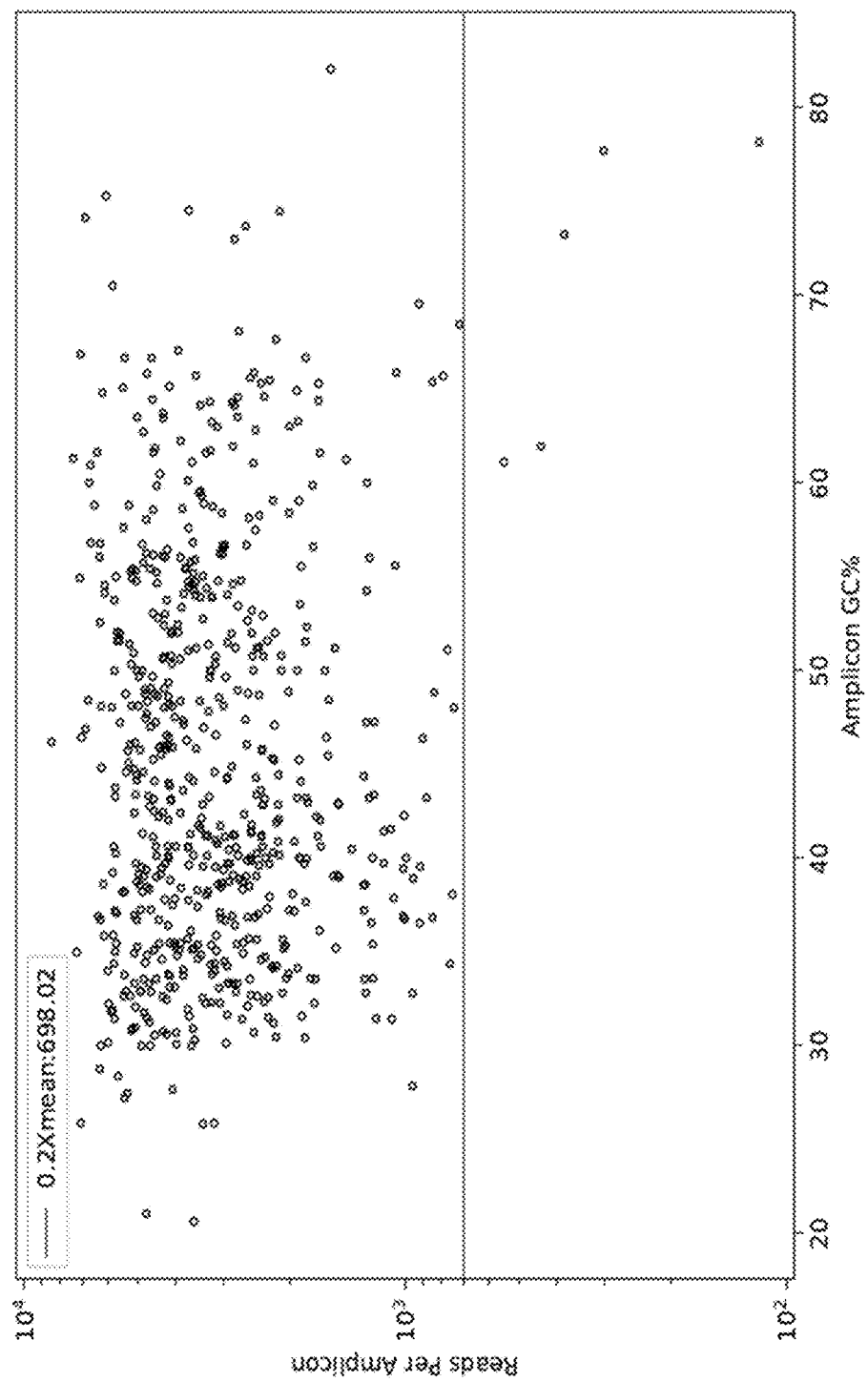
FIGS. 11A-11C illustrate GC bias and removing non-specific PCR products in the methods described herein.

Uniformity is a measure of how well every amplicon in a library is equally amplified in a multiplex PCR reaction. In order words, it measures the difference of copy numbers of amplicons between the under-amplified amplicons and the over-amplified amplicons. We found that the 40-plex panel and 205-plex panel used in Example 1 and 2 did not properly measure the uniformity. These two panels easily generated highly uniform libraries (FIG. 18, table 1). The number of amplicons defined by these panel were not sufficiently large to accommodate various kinds of easy and difficult-to-amplify amplicons. We then used a panel of 629 pairs of primer and made libraries with the reagent used above. We sequenced these libraries at mean reads around 700. The uniformity measured at 0.2× mean reads was larger than 99%, while uniformity at 0.5× mean reads was higher than 87%. Furthermore, amplicons with GC content from over 20% to 80% were equally amplified. Three amplicons covering parts of TERT promoter region that had 70-80% GC, which are well-known to be hard-to-amplify targets, were also amplified to lower multiples (FIG. 11A).

Figure 11B:
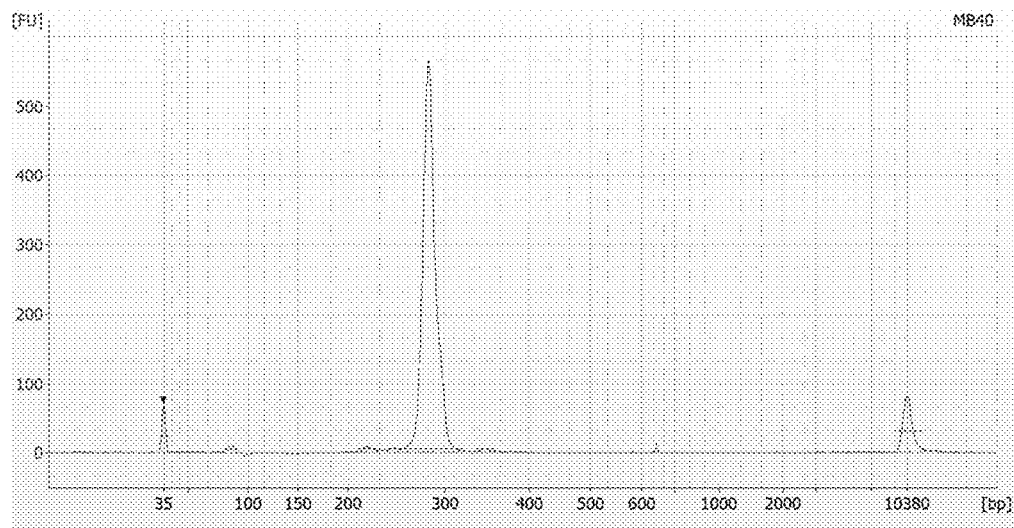
Figure 11C:
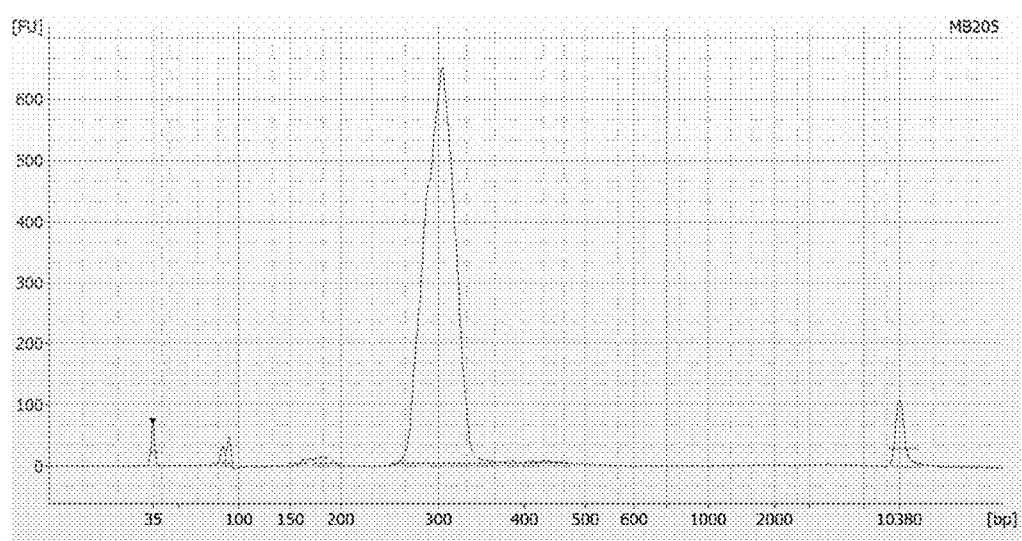

To demonstrate the removal of non-specific amplification products and scalability of our method, we made libraries with 40-plex and 205-plex panels. These libraries were found to have less than 5% non-specific amplification products, measured with high-sensitivity DNA kit in BioAnalyzer 2100 (FIG. 11B).

Example 4. The Length of Molecular Barcode

We investigated the number of unique molecular barcodes that was required to label each molecule individually in different amounts of DNA targets. The number of DNA targets was defined by the amount of input DNA in nanograms and the number of primer pairs in a given primer panel. We calculated the probability (P) of the identical barcode to label two different DNA molecules under various circumstances, assuming barcode assignment was a generalized birthday problem, by using formula:

$$P = 1 - \left(1 - \frac{T}{2B}\right)^{(T-1)}$$

T is the number of total DNA targets, B is the total number of available molecular barcodes. We found that 12-40 random nucleotides in the molecular barcode cassette was necessary and sufficient to label every DNA molecules, with no duplication of barcodes, under most extreme low and high circumstances of the number of DNA targets.

Figure 12:
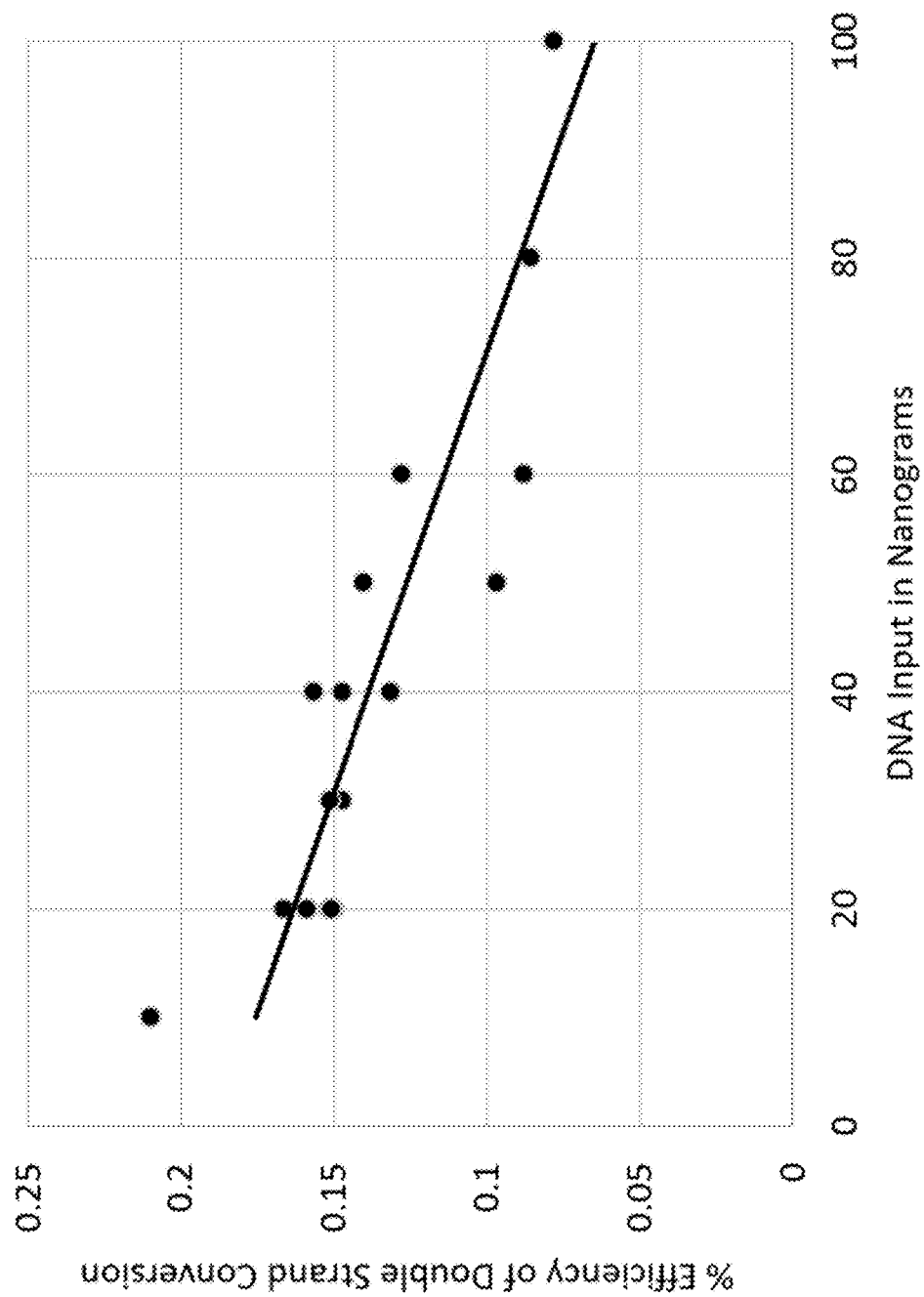
FIG. 12 shows evidence that molecular barcode of 12 random nucleotides was insufficient for the increasing amounts of DNA input. With 12 random nucleotides as molecular barcode, there was a declining efficiency of double strand conversion with increasing amounts of DNA input.

To demonstrate that sufficient numbers of molecular barcodes were required to label different amount target DNA, we made libraries with 10-100 ng input DNA of 0.2% NA12878/NA12877. These libraries were made with a 40-pair primer panel. Each primer contained a molecular barcode cassette with 12 random nucleotides. After sequencing, we counted the numbers of barcodes that could be sorted into sense and anti-sense strand of target DNA in each library. These numbers were compared with the theoretical numbers derived from the amounts of input DNA. This gave the efficiency of double strand conversion of molecular barcodes. We found the efficiency was inversely related to the amounts of input DNA at molecular barcode length of 12 (FIG. 12). This indicated that some identical barcodes were assigned onto different DNA molecules with increased DNA inputs. In order words, if an insufficient number of molecular barcodes was used to label a relatively large number of DNA targets, then some different DNA targets would share identical molecular barcodes. This resulted in apparently low recovery of unique molecular barcodes in the sequence analysis.

Example 5. Amount of Input DNA, Cycle Number and Yield

Figure 13:
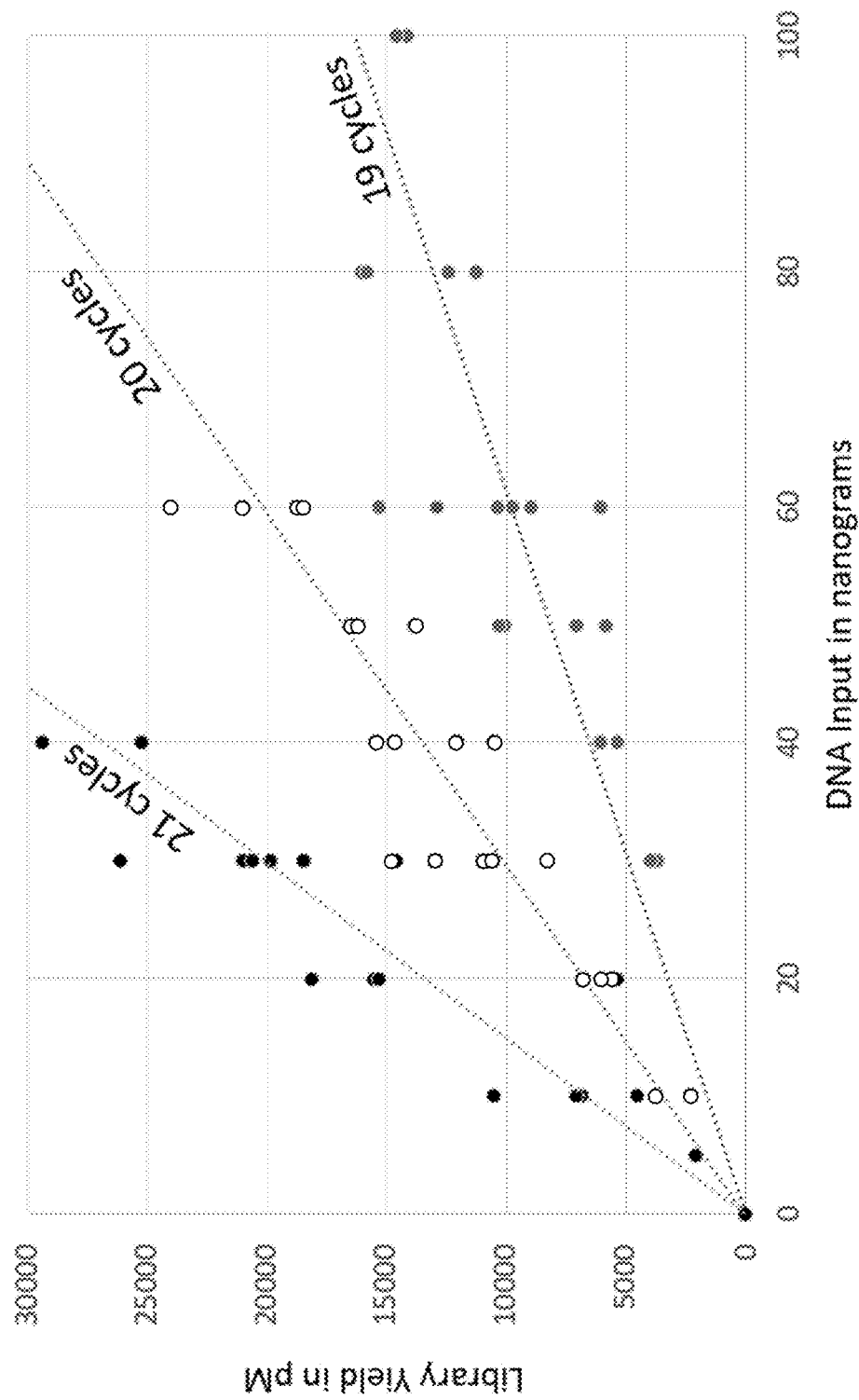
FIG. 13 illustrates required cycles of PCR for the specified amount of DNA input and resulting yield of library; the relationship between the amount of DNA input and number of cycles may be used to help achieve a library yield desired (e.g., between 10,000 to 25,000 pM).

Our method uses 3 cycles of multiplex PCR to add molecular barcodes onto DNA targets. The quantities of these targets are amplified in the second PCR. The relationship among the amount of input DNA, cycle number of the second PCR, and the library yields are presented in FIG. 13. Libraries with yields within 10,000-25,000 pM were used for sequencing. Libraries with concentration over 25,000 pM were seldom used for concerns of over-amplification.

Example 6. Sequencing Depth, Total Reads Required

The required sequencing depth for a library can be viewed as the number of reads, usually in millions, required for every target of the library to be sequenced a specified number of times. Firstly, it should be large enough to allow every target in the library to be sequenced. Secondly, it should be even larger so that every target is sequenced a specified number of times. To know the required sequencing depth for a specified library, we first need to know the number of unique targets in the library. We can estimate the total available number of targets from the amount of input DNA and the number of primer pairs of the primer panel. A fraction of this number is amplified by PCR. We know this fraction through the efficiency of PCR. We should also consider that some different targets may be taken as identical targets if an insufficient number of molecular barcodes are used. Finally, only a fraction of the targets can be sorted into sense and anti-sense strands of the original targets (the efficiency of double strand conversion). This is caused by the following two major problems. First, some molecular barcodes may become damaged during the workflow from library to sequencing, resulting in the loss of some targets. Second, the two strands of a DNA target may be unevenly amplified, leading to failed grouping of both strands in the sequence analysis.

With these problems in mind, we sequenced a large number of libraries at various sequencing depth. These libraries were made with 10 to 100 ng of 0.2% of NA2878/NA12877, and the 40 plex primer panel with 12 random nucleotides as molecular barcodes. Considering that the number of molecular barcodes might be insufficient for high input libraries and cause inaccurate interpretation, we calculated the efficiency of double strand conversion. We selected a group of 39 samples with close conversion efficiencies (average 14%, standard deviation of 3%) for further analysis (FIG. 14A).

The sequencing depth of each library was expressed as the number of reads per unique barcode qualified for double strand grouping. As expected, with higher sequencing depth, reads per amplicon also increased (FIG. 14B). To find the optimal sequencing depth, we calculated the ratio of reads used in double strand grouping to on-target reads. When plotted against sequencing depth, we found that the highest ratio corresponded to double strand grouping with 12-16 members for each unique barcode (FIG. 14C). In this range, the reads in each unique barcode family formed a normal distribution (FIG. 14D). Based on the above results, we found that 12000 paired end reads were required per nanogram of input DNA per amplicon. E further found that the PCR efficiency was 53.4%, counting the recovered total number of unique molecular barcodes to the calculated total number of input molecules.

Example 7. Base Bias

Figure 15A:
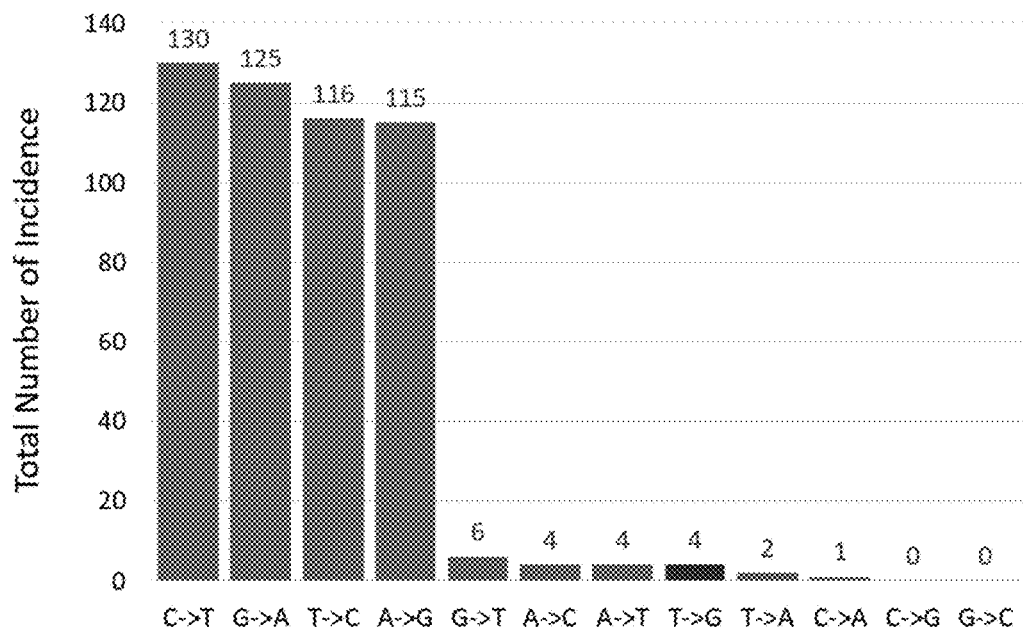
FIGS. 15A-15B illustrate base bias of random errors detected by single strand consensus. Forty (40) ng of DNA was used. The higher numbers of transitions (FIG. 15A) were found, but the frequencies of these transitions were not elevated (FIG. 15B). The high frequency of T→G transformation occurred four times in this samples.
Figure 15B:
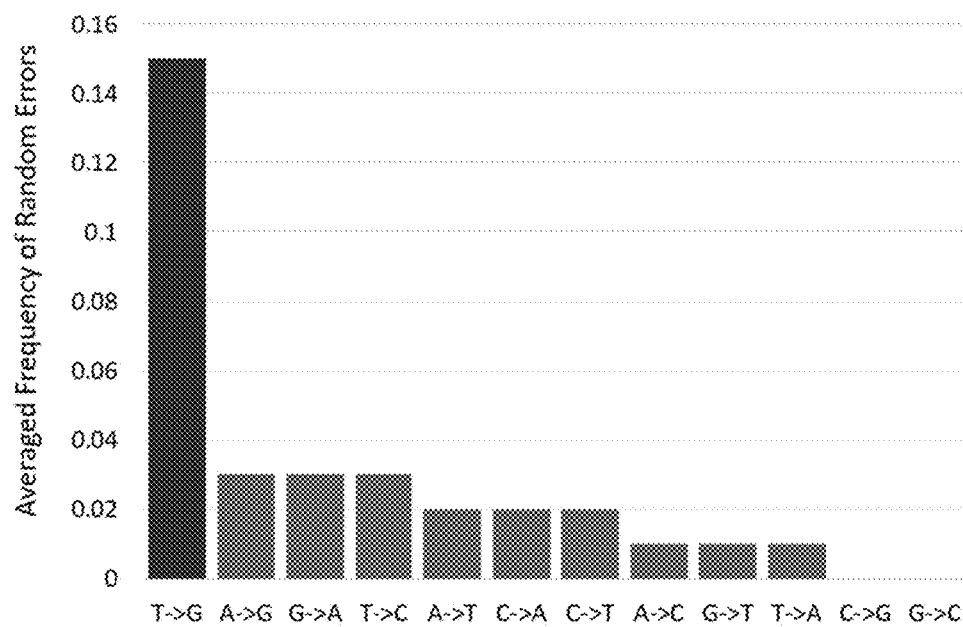

We next identified if our method produced any base bias. This was done by counting the types of base changes in all of the random errors left over after consensus analysis. These base changes represent the "random noise" that occurred in our method and the sequencing process. We found there were less than 20 random errors after double strand consensus with input DNA up to 50 ng of DNA, 30 with up to 100 ng of input DNA. We did not find any difference in frequency of the 12 types of bases changes, nor statistically significant difference in the number of these types of base changes. We then analyzed all of the nucleotides called from single strand consensus, except for the known variants, in a library made with 40 ng of DNA. We found the number of G/C→T/A and T/A→C/G transitions were significantly higher than the rest kinds of mutations (FIG. 15A). As expected, these transitions are commonly found in PCR based methods. We further found that the frequencies of these transitions were similar to other types of mutations, indicating these mutations happened randomly across the entire target regions (FIG. 15B). In other words, the random errors did not cluster at any specific location of the target regions.

Example 8. Removing Random Errors

Figure 16:
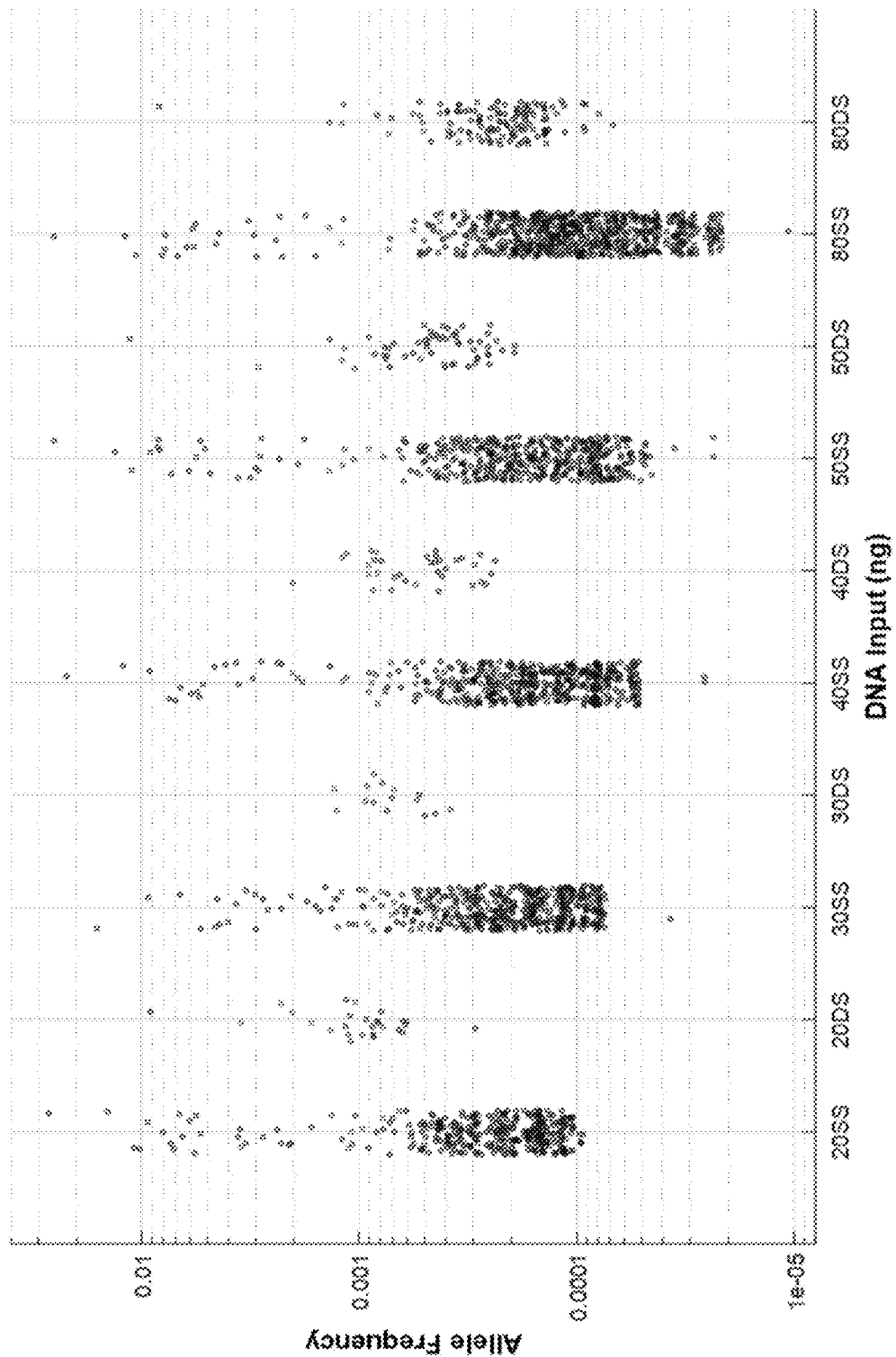
FIG. 16 illustrates the effect of removing random errors with various amount of DNA input.

The effect of double strand consensus to remove random errors from libraries made with 10 to 100 ng of DNA is shown in FIG. 16. We calculated consensus from single strand and tried to use it to remove random errors, however, large numbers of random errors still existed. Due to the error rate of the method, it showed a trend that more random errors were left when increased amount of DNA was used to make the library. When double strand consensus was used, the number of random errors were significantly reduced from all samples.

Example 9. Error Rate

Error rate was calculated as the number of random errors after filtering by double strand consensus, out of the total sequenced on-targets nucleotides. To avoid miscalculation due to insufficient number of molecular barcodes used, we used libraries made with 10-20 ng of input DNA. At the highest efficiency of double strand conversion, the error rate was estimated to be $8.2 \times 10^{\wedge}-8$ per base on average.

Example 10. Efficiency, Sensitivity and Amplicon Length

We used digested gDNA to simulate cfDNA. The digested gDNA was size selected to closely resemble the length of cfDNA. PCR efficiency was 53.4% for both digested DNA and gDNA. In order to effectively amplify short fragment of DNA, such as cfDNA, we designed the primer panel to amplify amplicons of 70-90 nucleotide in length, with average of 79 nucleotides. The theoretical efficiency of amplifying 166 bp DNA fragments was estimated to be 52.4% by using the formula:

$$eff = 1 - \frac{\text{amplicon length}}{\text{target length}}$$

Efficiency of double strand conversion was 20% for both digested gDNA and gDNA.

Figure 17:
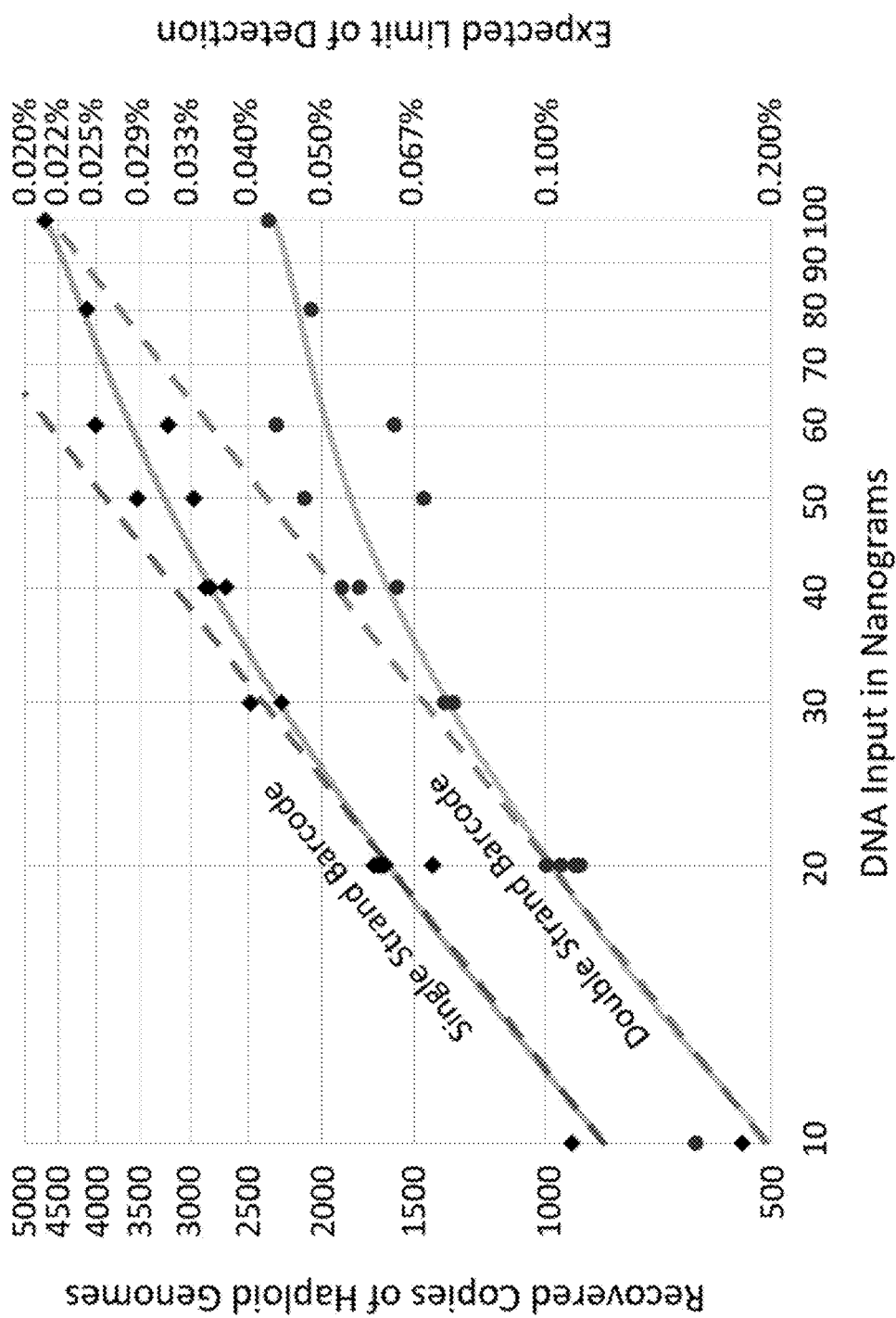
FIG. 17 illustrates recovery of copies of haploid genomes in sequencing with various amounts of input DNA. The solid lines are the detected copies of haploid genomes after consensus by single strand and double strand, respectively. The dashed lines are expected numbers. The curved lines suggest insufficient number of molecular barcodes were used in these samples, especially with the larger amounts of input DNA.

Sensitivity was evaluated by the number of haploid genomes recovered after double strand consensus. As shown in FIG. 17, 20 ng of input DNA was required to recover 1000 copies of haploid genomes, enabling the detection of 1 mutant in 1000 targets (0.1% limit of detection). We expected a linear relationship between the input DNA and the recovered copies of haploid genomes, shown by the dashed line in FIG. 17. However, we found that fewer and fewer copies of haploid genomes were recovered with increasing input of DNA. These samples were labeled with molecular barcodes with only 12 random nucleotides. In our calculation, there was 100% chance for two different DNA molecules to share an identical barcode when using 12-base long molecular barcodes for 10 ng of input DNA and 40 pairs of primers. We believe that the nonlinear relationship was caused by insufficient number of nucleotides in each molecular barcode, especially when larger amount of input DNA was used. Better limit of detection should be possible with longer random nucleotide region in the molecular barcode cassette.

Example 11. Variant Calling of GDNA with Spike-Ins

The sensitivity and positive prediction value (PPV) are presented in FIG. 20A-20B. We spiked reference DNA HD780 into NA12877 at 0.2% allele frequency. There were 8 mutation sites of HD780, including one insertion and one deletion. All of these 8 mutation sites were detected with 20 ng DNA input, and 4 were detected with 10 ng DNA input (FIG. 21A). We also diluted NA12878 into NA12877 at 0.2% concentration. We looked into 8 unique allele sites of NA12878 at 0.1% allele frequency. All of these 8 mutation sites were detected with 20 ng DNA input, and 7 were detected with 10 ng DNA input (FIG. 21B).

Any of the methods described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc.

Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of reducing redundant molecular barcodes from a template-dependent primer extension reaction, the method comprising:
   amplifying a plurality of target nucleic acids using a plurality of pairs of primers that are in a same reaction mixture for three cycles to form a plurality of double-stranded target-specific amplification DNA fragments, wherein each primer pair in said plurality of pairs of primers comprises a forward primer and a reverse primer and both the forward primer and the reverse primer include a molecular barcode cassette having a molecular barcode region comprising a 12-40 random nucleotide sequence that is positioned between a 5' end fixed nucleotide sequence region and a 3' end fixed nucleotide sequence region;
   introducing, following the third cycle, one or a mix of single-stranded DNA specific exonucleases to cleave one or more single-stranded DNA regions on a 5' terminus and a 3' terminus of double-stranded target-specific amplification DNA fragments, wherein the single-stranded DNA regions comprise unmatched base pairs at either terminus of the double-stranded target-specific amplification DNA fragments, leaving a plurality of amplification products with double-stranded DNA termini and intact molecular barcode cassettes on both ends; and
   amplifying the plurality of amplification products with intact molecular barcode cassettes on both ends with a pair of primers that are complimentary to the 5' end fixed nucleotide sequence region of the molecular barcode cassette.

2. The method of claim 1, wherein the unmatched base pairs at either terminus of the double-stranded target-specific amplification DNA fragments are derived from the random nucleotides of the molecular barcode region and the 5' end fixed nucleotide sequence region of the molecular barcode cassette.

3. The method of claim 1, wherein the 5' end fixed nucleotide sequence comprises any number and type of nucleotides.

4. The method of claim 1, wherein introducing comprises introducing the one or the mix of single-stranded DNA specific exonucleases before further amplification.

5. The method of claim 1, wherein introducing the one or a mix of single-stranded DNA specific exonucleases comprises introducing a resolvase, an exonuclease, multiple exonucleases, or a combination of exonucleases and nucleases, selected from the group comprising: T4 endonuclease VII, T7 endonuclease I, S1 nuclease, P1 nuclease, CelI nuclease, mung bean nuclease, exonuclease VII, RecJ, RecJf.

6. The method of claim 1, further comprising removing single-stranded DNA fragments that are cleaved by the one or a mix of single-stranded DNA specific exonucleases.

7. The method of claim 1, further amplifying the plurality of amplification products with a pair of primers that are complimentary to the 5' end fixed nucleotide sequence region of the molecular barcode cassette comprises amplifying by polymerase chain reaction.

8. The method of claim 1, further comprising analyzing the amplification products by high-throughput sequencing.

9. The method of claim 1, further comprising analyzing and sorting the random nucleotide sequences of the amplification products, grouping identical and similar sequences of molecular barcodes into families of molecular barcodes, validating the length and sequence of each molecular barcode in each family of molecular barcodes, and removing amplification products with disqualified nucleotide sequences of molecular barcodes.

10. The method of claim 8, further comprising analyzing a consensus sequence of DNA targets from each family of molecular barcodes, removing random errors from each family of molecular barcodes, finding all sequences from the sense strand, finding all sequences from the antisense strand, finding variant frequency in a pool of sense strands, finding variant frequency in a pool of antisense strands, confirmation of variant frequency in both sense and antisense strands, and removing random errors from both sense and antisense strands.

11. The method of claim 1, wherein amplifying the plurality of target nucleic acids comprises performing a multiplex polymerase chain reaction.

12. The method of claim 1, wherein the plurality of target nucleic acids comprises DNA or RNA.

13. The method of claim 1, wherein the plurality of target nucleic acids is genomic DNA, cDNA, DNA purified from Formalin-fixed, Paraffin-embedded (FFPE) tissue samples (FFPE DNA), cell-free DNA (cfDNA) or circulating tumor DNA (ctDNA).

14. The method of claim 1, wherein the forward primer and a reverse primer each includes a target-specific primer that is from 8-50 nucleotides.

15. The method of claim 1, wherein the plurality of pairs of primers comprise at least 7 pairs of target-specific primers.

16. The method of claim 1, wherein said plurality of pairs of primers comprise between 7 pairs of target-specific primers and 1,000,000 pairs of target-specific primers.

17. The method of claim 1, wherein each primer of the plurality of pairs of primers includes a target-specific region of comprising one or more of: unmodified oligonucleotides with no chemical modifications of nucleotides, and chemical bonds and no degenerated bases.

18. The method of claim 1, wherein each primer of the plurality of pairs of primers includes a target-specific region of comprising modified oligonucleotides with one or more of: chemical modifications of nucleotides or chemical bonds, and degenerated bases.

19. The method of claim 1, wherein introducing one or a mix of single-stranded DNA specific exonucleases comprises introducing between about 0.2 U and 1000 U of exonuclease for between 0.5 minutes and 60 minutes at between 16° C. and 37° C.

20. The method of claim 1, wherein introducing the one or a mix of single-stranded DNA specific exonucleases comprises introducing a single-stranded DNA specific nuclease or single-stranded DNA specific exonuclease comprising one or more of: a nuclease S1, a nuclease P1, a mung bean nuclease, a CEL I nuclease, an endonuclease CEL I, an exonuclease I, an exonuclease V, an exonuclease VII, an RecJ, an RecJf, and combinations, fusions, or mutations thereof.

21. A method of reducing redundant molecular barcodes from a template-dependent primer extension reaction, the method comprising:

amplifying a plurality of target nucleic acids using a plurality of pairs of primers that are in a same reaction mixture for three cycles to form a plurality of double-stranded target-specific amplification DNA fragments, wherein each primer pair in said plurality of pairs of primers comprises a forward primer and a reverse primer, each having a 5' end fixed nucleotide sequence region, and either the forward primer or the reverse primer includes a molecular barcode cassette having a molecular barcode region comprising a 12-40 random nucleotide sequence that is positioned between the 5' end fixed nucleotide sequence region and a 3' end fixed nucleotide sequence region;

introducing, following the third cycle, one or a mix of single-stranded DNA specific nucleases and resolvases to cleave: (i) heteroduplex regions of unmatched base pairs derived from the random nucleotides of molecular barcodes of the double-stranded target-specific amplification DNA fragments, and (ii) single-stranded DNA regions on a 5' terminus and a 3' terminus of the double-stranded target-specific amplification DNA fragments, wherein the single-stranded DNA regions comprise unmatched base pairs at either terminus that are derived from the random nucleotides of the molecular barcode region and the 5' end fixed nucleotide sequence region of the molecular barcode cassette, leaving a plurality of amplification products with intact molecular barcode cassettes on either ends; and amplifying the plurality of amplification products with intact molecular barcode cassettes on either ends with a pair of primers that are complimentary to the 5' end fixed nucleotide sequence region of the molecular barcode cassette.

* * * * *

SEQUENCE LISTING

<160> NUMBER OF SEQ ID NOS: 7

<210> SEQ ID NO 1
<211> LENGTH: 29
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 1
aatgatacgg cgaccaccga gatctacac                                    29

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acactctttc cctacacgac gctcttccga tct                               33

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caagcagaag acggcatacg agat                                         24

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtgactggag ttcagacgtg tgctcttccg atct                              34

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aggaattaag agaagc                                                  16

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atggccagcg tggccagcgt gg                                           22

<210> SEQ ID NO 7
<211> LENGTH: 13
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 7
atggccagcg tgg                                                        13
```